(12) United States Patent
Young et al.

(10) Patent No.: US 11,408,023 B2
(45) Date of Patent: Aug. 9, 2022

(54) MICROBIAL DETECTION DEVICES INCLUDING ADHESIVE MASKED NUTRIENTS AND METHODS OF USING THE SAME

(71) Applicant: 3M INNOVATIVE PROPERTIES COMPANY, St. Paul, MN (US)

(72) Inventors: Alexi J. Young, Shoreview, MN (US); Evan D. Brutinel, Inver Grove Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 344 days.

(21) Appl. No.: 16/461,397

(22) PCT Filed: Dec. 22, 2017

(86) PCT No.: PCT/US2017/068213
§ 371 (c)(1),
(2) Date: May 16, 2019

(87) PCT Pub. No.: WO2018/125805
PCT Pub. Date: Jul. 5, 2018

(65) Prior Publication Data
US 2020/0056219 A1     Feb. 20, 2020

Related U.S. Application Data

(60) Provisional application No. 62/439,671, filed on Dec. 28, 2016.

(51) Int. Cl.
*C12Q 1/04* (2006.01)
*C12M 1/12* (2006.01)
(Continued)

(52) U.S. Cl.
CPC ............ *C12Q 1/04* (2013.01); *C12M 23/04* (2013.01); *C12M 25/02* (2013.01); *C12M 33/02* (2013.01); *C12Q 1/06* (2013.01)

(58) Field of Classification Search
CPC ............ C12Q 1/04; C12Q 1/06; C12M 25/02; C12M 23/04; C12M 33/02
See application file for complete search history.

(56) References Cited

U.S. PATENT DOCUMENTS 4,565,783 A * 1/1986 Hansen .................. C12Q 1/04
435/30
5,089,413 A * 2/1992 Nelson ................... C12M 23/04
435/254.1
(Continued)

FOREIGN PATENT DOCUMENTS

CN     102363802     2/2012
CN     105754849     7/2016
(Continued)

OTHER PUBLICATIONS

International Search report for PCT International Application No. PCT/US2017/068213 dated Mar. 26, 2018, 4 pages.
(Continued)

*Primary Examiner* — Sean C. Barron
(74) *Attorney, Agent, or Firm* — Adrian L. Pishko

(57) ABSTRACT

Devices for microbial detection of microorganisms are provided including a body member including a substrate having a first major surface and a second major surface. The device further includes a substantially dry, first microbial growth nutrient composition disposed on a portion of the first major surface, a first adhesive composition adhered to the first microbial growth nutrient composition, and a cold-water-soluble first hydrogel-forming composition adhered to the first adhesive composition. The device also includes a cover sheet attached to the body member, where the cover sheet
(Continued)

includes a first major surface facing the body member. Devices including a water-proof pouch are also provided. Methods for detecting and enumerating at least one microorganism in a sample are additionally provided, using the devices.

16 Claims, 7 Drawing Sheets

(51) Int. Cl.
*C12Q 1/06* (2006.01)
*C12M 1/30* (2006.01)

(56) References Cited

U.S. PATENT DOCUMENTS

| | | | |
|---|---|---|---|
| 5,232,838 A | 8/1993 | Nelson | |
| 5,364,766 A | 11/1994 | Mach | |
| 5,409,838 A | 4/1995 | Wickert | |
| 5,443,963 A | 8/1995 | Lund | |
| 5,462,860 A | 10/1995 | Mach | |
| 5,601,998 A | 2/1997 | Mach | |
| 5,635,367 A | 6/1997 | Lund | |
| 5,681,712 A | 10/1997 | Nelson | |
| 5,723,308 A | 3/1998 | Mach | |
| 5,869,321 A | 2/1999 | Franklin | |
| 6,632,661 B2 | 10/2003 | Wickert | |
| 6,649,406 B1* | 11/2003 | Williams | C12M 23/04 435/39 |
| 6,770,454 B2* | 8/2004 | Reilly | C12Q 1/04 435/30 |
| 7,087,401 B2 | 8/2006 | Sandberg | |
| 7,371,464 B2 | 5/2008 | Sherman | |
| 7,695,818 B2 | 4/2010 | Sherman | |
| 8,357,498 B2 | 1/2013 | Ushiyama | |
| 8,889,351 B2 | 11/2014 | Mach | |
| 8,921,067 B2 | 12/2014 | Chandrapati | |
| 2012/0028297 A1 | 2/2012 | Zook | |
| 2012/0107913 A1 | 5/2012 | Baba | |
| 2013/0084624 A1 | 4/2013 | Waku | |
| 2014/0220610 A1* | 8/2014 | Chandrapati | C12M 23/20 435/21 |
| 2015/0329894 A1 | 11/2015 | Roscoe | |
| 2016/0032231 A1 | 2/2016 | Chandrapati | |

FOREIGN PATENT DOCUMENTS

| | | |
|---|---|---|
| JP | 08336381 | 12/1996 |
| JP | H 11-513248 T2 | 11/1999 |
| JP | 2007124985 | 5/2007 |
| JP | 2013-532980 | 8/2013 |
| JP | 2015-524280 | 8/2015 |
| WO | WO 1995-20674 | 8/1995 |
| WO | WO 1996-38533 | 12/1996 |
| WO | WO 1997-011157 | 3/1997 |
| WO | WO 2001-038559 | 5/2001 |
| WO | WO 2002-046353 | 6/2002 |
| WO | WO 2010-147918 | 12/2010 |
| WO | WO 2011-007802 | 1/2011 |
| WO | WO 2012-012106 | 1/2012 |
| WO | WO 2012-012172 | 1/2012 |
| WO | WO 2014-018433 | 1/2014 |
| WO | WO 2014-025514 | 2/2014 |
| WO | WO 2014-121243 | 8/2014 |
| WO | WO 2014-182586 | 11/2014 |
| WO | WO 2015-061213 | 4/2015 |
| WO | WO 2015-134686 | 9/2015 |
| WO | WO 2016-028839 | 2/2016 |
| WO | WO 2016-176173 | 11/2016 |
| WO | WO 2017-019345 | 2/2017 |
| WO | WO 2018-125811 | 7/2018 |

OTHER PUBLICATIONS

International Search report for PCT International Application No. PCT/US2017/068233 dated Apr. 11, 2018, 5 pages.

* cited by examiner

MICROBIAL DETECTION DEVICES INCLUDING ADHESIVE MASKED NUTRIENTS AND METHODS OF USING THE SAME

CROSS REFERENCE TO RELATED APPLICATIONS

This application is a national stage filing under 35 U.S.C. 371 of PCT/US2017/068213, filed Dec. 22, 2017, which claims the benefit of U.S. Application No. 62/439,671, filed Dec. 28, 2016, the disclosures of which are incorporated by reference in their entirety herein.

FIELD

The disclosure relates to devices useful for the growing and detection of microorganisms, including microbial growth nutrients. This disclosure also relates to methods of detecting or enumerative microorganisms using the devices.

BACKGROUND

A wide variety of culture devices have been developed. As one example, culture devices have been developed by 3M Company (hereafter "3M") of St. Paul, Minn. In particular, culture devices are sold by 3M under the trade name PETRIFILM plates. Culture devices can be utilized to facilitate the rapid growth and detection of microorganisms commonly associated with food contamination, including, for example, aerobic bacteria, *E. coli*, coliforms, enterobacteria, yeast, mold, *Staphylococcus aureus*, *Listeria*, *Campylobacter*, and the like. The use of PETRIFILM plates, or other growth media, can simplify bacterial testing of food samples, for instance.

Culture devices can be used to enumerate or identify the presence of bacteria so that corrective measures can be performed (in the case of food testing) or proper diagnosis can be made (in the case of medical use). In other applications, culture devices may be used to rapidly grow microorganisms in laboratory samples, e.g., for experimental purposes.

SUMMARY

Devices and methods for the propagation or storage of microorganisms are provided. In a first aspect, a device is provided. More particularly, a device is provided including a body member including a substrate having a first major surface and a second major surface. The device further includes a substantially dry, first microbial growth nutrient composition disposed on a portion of the first major surface, a first adhesive composition adhered to the first microbial growth nutrient composition, and a cold-water-soluble first hydrogel-forming composition adhered to the first adhesive composition. The device also includes a cover sheet attached to the body member, where the cover sheet includes a first major surface facing the body member.

In a second aspect, another microbial detection device is provided. The microbial detection device includes a water-proof pouch including a first wall portion having an inner surface and an outer surface, a second wall portion having an inner surface and an outer surface, and a porous membrane filter disposed in the pouch between the inner surface of the first wall portion and the inner surface of the second wall portion. The membrane filter has a first major surface and a second major surface opposite the first major surface. The water-proof pouch further includes a first compartment defined in part by the inner surface of the first wall portion and defined in part by the first major surface of the membrane filter and a sealable sample port that provides access to deposit a liquid into the first compartment. Additionally, the water-proof pouch includes a second compartment defined in part by the inner surface of the second wall portion and defined in part by the second major surface of the membrane filter, and an absorbent pad disposed in the second compartment. The membrane filter permits passage of aqueous liquids from the first compartment to the second compartment and prevents passage of particles of a predetermined size from the first compartment to the second compartment. The water-proof pouch also includes a substantially dry microbial growth nutrient composition disposed on a portion of the pouch in the first compartment, an adhesive composition adhered to the microbial growth nutrient composition, and a cold-water-soluble hydrogel-forming composition adhered to the adhesive composition.

In a third aspect, a method of detecting and enumerating at least one microorganism in a sample is provided. The method includes providing a device according to the first aspect, separating the first layer from the second layer, and adding a predetermined volume of a sample containing at least one microorganism onto the first hydrogel-forming composition to form an inoculated device. The method further includes contacting the first layer back to the second layer, incubating the inoculated device, and detecting the presence or an absence of a colony of the target microorganism in the device.

In a fourth aspect, another method for detecting and enumerating at least one microorganism in a sample is provided. The method includes providing a device according to the second aspect, placing a predetermined volume of aqueous sample into the first compartment of the device, sealing the sample port, incubating the device, and detecting the presence or an absence of a colony of the target microorganism in the device.

The devices and methods allow for simple and rapid detection of microorganisms.

While the above-identified drawings, which may not be drawn to scale, set forth various embodiments of the present disclosure, other embodiments are also contemplated, as noted in the Detailed Description.

DETAILED DESCRIPTION

Devices and methods of propagating or storing a microorganism are provided.

The recitation of any numerical range by endpoints is meant to include the endpoints of the range, all numbers within the range, and any narrower range within the stated range (e.g. 1 to 5 includes 1, 1.5, 2, 2.75, 3, 3.8, 4, and 5). Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example, the expression "A and/or B" means A, B, or a combination of A and B.

"Cluster" refers to a group of agglomerated and/or aggregated particles.

"Agglomerated" refers to a weak association of primary particles or aggregated particles usually held together by charge or polarity. Agglomerated particles can typically be broken down into smaller entities by, for example, shearing forces encountered during dispersion of the agglomerated particles in a liquid. The terms "aggregated" and "aggregates" refer to a strong association of primary particles often bound together by, for example, residual chemical treatment, covalent chemical bonds, or ionic chemical bonds. Further breakdown of the aggregates into smaller entities is very difficult to achieve.

"Cold-water-soluble" refers to material which forms a solution in water at room temperature (i.e., about 25° C.).

"Hydrophobic" refers to a material that exhibits a water contact angle of 90° or larger on its surface.

"Opaque" refers to a substrate having at most 10% light transmission.

"Powder" refers to a finely divided particulate material having an average diameter in a range from 0.1 micrometer up to 400 micrometers.

"Reconstituted medium" refers to a solution or gel formed from the reconstitution of a cold-water-soluble powder with an aqueous liquid.

"Substantially impermeable to microorganisms and water vapor", as used herein, refers to a cover sheet that prevents undesired contamination and hydration of underlying layers of cold-water-soluble powder during shipping, storage, and use of thin film culture device(s), and avoids desiccation of the reconstituted medium, such that the reconstituted medium is suitable to support the growth of microorganisms during an incubation period.

"Substantially water-free", as used herein, designates a water content no greater than about the water content of the ambient environment.

"Test sample", as used herein, refers to a component or portion taken from a food product, a human or animal test subject, pharmaceutical or cosmetic commodity, soil, water, air or other environmental source, or any other source from which a presence and, optionally, an enumeration of aerobic and/or aerotolerant bacteria is to be determined. A test sample may be taken from a source using techniques known to one skilled in the art including, for example, pouring, pipetting, swabbing, filtering, and contacting. In addition, the test sample may be subjected to various sample preparation processes known in the art including, for example, blending, stomaching, homogenization, enrichment, selective enrichment, or dilution.

"Transparent" refers to a substrate having at least 90% light transmission.

Devices for the propagation and/or storage of microorganisms are provided having advantageous features such as controlling the amount of nutrients included in the device. Further, the nutrients are not directly exposed to samples during use, and thus are protected from potentially washing off when a fluid sample is introduced into the device.

In a first aspect, a device is provided. More particularly, a device is provided including a body member including a substrate having a first major surface and a second major surface. The device further includes a substantially dry, first microbial growth nutrient composition disposed on a portion of the first major surface, a first adhesive composition adhered to the first microbial growth nutrient composition, and a cold-water-soluble first hydrogel-forming composition adhered to the first adhesive composition. The device also includes a cover sheet attached to the body member, where the cover sheet includes a first major surface facing the body member. In any embodiment, the substantially dry, first microbial growth nutrient composition may be disposed in the form of a layer on a portion of the first major surface, the first adhesive composition may be in the form of a layer adhered to the first microbial growth nutrient composition, the cold-water-soluble first hydrogel-forming composition may be in the form of a layer adhered to the first adhesive composition, wherein the first adhesive composition layer is located between the first microbial growth nutrient composition layer and the cold-water-soluble first hydrogel-forming composition layer.

Figure 1:
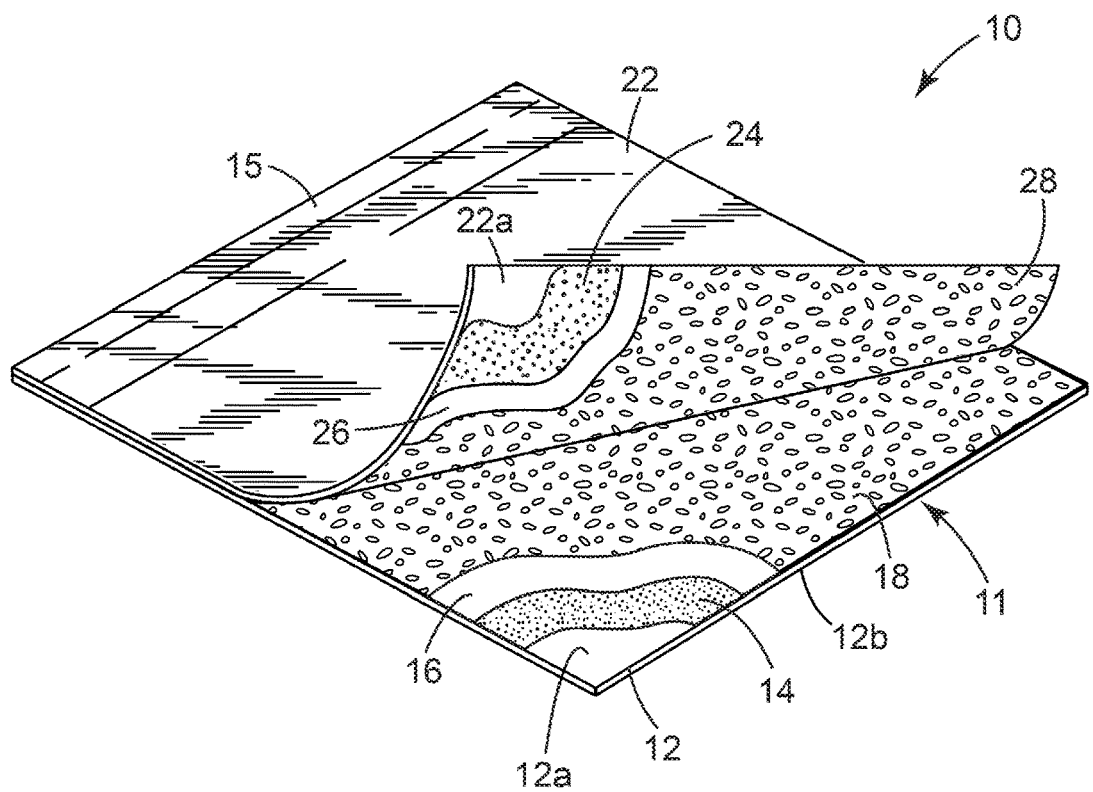
FIG. 1 is a top perspective view, partially in section, of an exemplary embodiment of a microbiological growing device.

FIG. 1 illustrates an exemplary embodiment of a device for growing microorganisms. The device 10 includes a body member 11 comprising a substrate 12 having a first major surface 12a (e.g., upper surface) and a second major surface 12b (e.g., lower surface). Moreover, the device 10 also includes a cover sheet 22 attached to the body member 11. The cover sheet 22 includes a first major surface 22a facing the body member 11.

Figure 4:
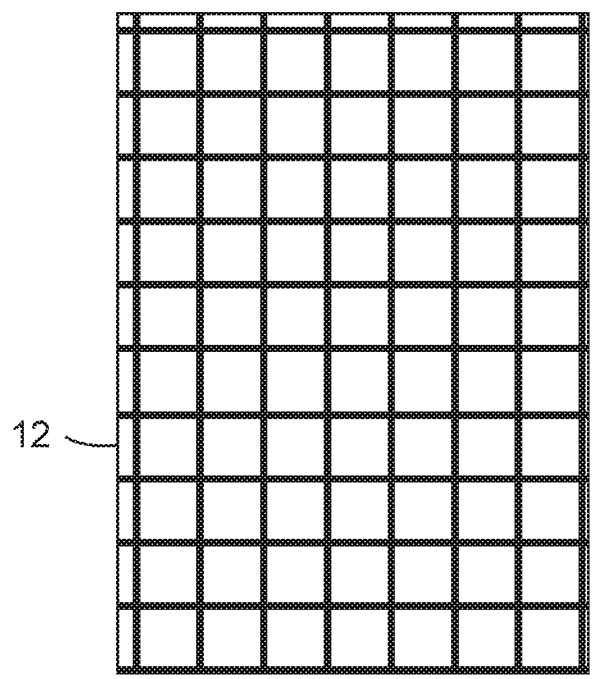
FIG. 4 is a top view of the device of FIG. 2 showing a grid pattern printed on the substrate layer.
Figure 5:
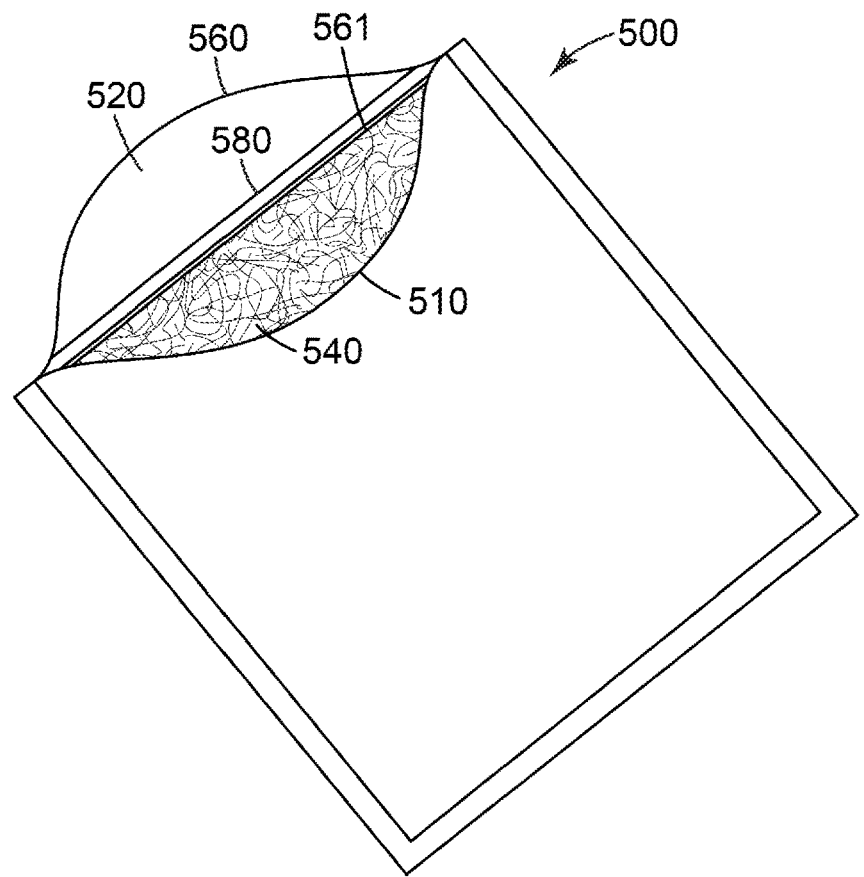
FIG. 5 is a perspective view of a further exemplary device according to the present disclosure.

The substrate 12 is water-proof, and is optionally a self-supporting water-proof substrate. In some embodiments, the substrate 12 is a film of a material such as polyester, polypropylene, silicone, or polystyrene, which will not absorb or otherwise be affected by water. Polyester films and polypropylene films having a thickness from about 20 micrometers to about 250 micrometers, as well as polystyrene films having a thickness of about 380 micrometers, have each been found to be suitable for the substrate 12. Other suitable substrates include paper with a polyethylene or other water-proof coating. An example of a suitable polyethylene-coated paper substrate is "Schoeller Type MIL" photoprint paper (commercially available from Schoeller Pulaski, New York). The substrate 12 may be either transparent or opaque, depending on whether one wishes to view bacterial colonies through the substrate. In the exemplary embodiment shown in FIG. 4, the substrate 12 has a square grid pattern printed on the second major surface 12b to facilitate the counting of bacterial colonies.

The first major surface 12a comprises a substantially dry, first microbial growth nutrient composition 14 disposed on a portion of the first major surface 12a. The device includes the microbial growth nutrient composition at a coating weight of 2 milligrams per square inch or more (mg/in$^2$), 5 mg/in$^2$ or more, 10 mg/in$^2$ or more, 12 mg/in$^2$ or more, or 15 mg/in$^2$ or more; and at a coating weight of 50 mg/in$^2$ or less, 45 mg/in$^2$ or less, 40 mg/in$^2$ or less, 35 mg/in$^2$ or less, 30 mg/in$^2$ or less, 24 mg/in$^2$ or less, 22 mg/in$^2$ or less, 20 mg/in$^2$ or less, or 18 mg/in$^2$ or less. One suitable method for applying the microbial growth nutrient composition on the substrate includes preparing an aqueous solution or a suspension including at least the microbial growth nutrient composition, disposing a coating of the solution or suspension on the substrate surface, and drying the coating to form the substantially dry microbial growth nutrient composition. The skilled practitioner is capable of selecting a suitable coating method, including for instance and without limitation, knife-coating, gravure coating, curtain coating, air knife coating spray coating, die coating, draw bar coating or curtain coating or roll-coating. The coating is optionally dried at an elevated temperature (e.g., in a range from 50° C. to 100° C.) or in ambient conditions. In some embodiments, the microbial growth nutrient composition contains 75% by weight or more microbial growth nutrients, or 80% by weight or more, or 85% by weight or more, or 90% by weight or more, or 95% by weight or more microbial growth nutrients. Advantageously, in certain embodiments a greater amount of microbial growth nutrients can be included in the device than in devices in which the microbial growth nutrient composition is powder coated to an adhesive layer and/or combined with a substantial amount of a cold-water-soluble gelling agent.

A first adhesive composition 16 is adhered to the first microbial growth nutrient composition 14. The first adhesive composition 16 is (substantially) water-insoluble and non-inhibitory to the growth of microorganisms. In some embodiments, the first adhesive composition 16 is sufficiently transparent when wet to enable the viewing of bacterial colonies through the film coated with the adhesive. In some embodiments, the first adhesive composition 16 is a pressure-sensitive adhesive. In some other embodiments, heat-activated adhesives in which a lower melting substance is coated onto a higher melting substance may also be used. Water-activated adhesives such as mucilage may also be useful.

It has been unexpectedly discovered that despite the lack of compatibility between the materials of the microbial growth nutrient composition (e.g., being water soluble) and the adhesive composition (e.g., being water insoluble), a sufficient amount of nutrients are able to traverse through the layer of adhesive composition to be available for microorganism consumption in the device. Moreover, due to being covered (e.g., masked) by the first adhesive composition, the nutrients are not exposed on the surface of the film and thus are protected from washing off when a fluid sample is introduced into the device. This is particularly relevant for applications in which the sample must contact the powder layer and then pass through a filter (such as devices according to the second aspect of the present disclosure).

Referring again to FIG. 1, the device 10 further includes a cold-water-soluble first hydrogel-forming composition 18 adhered to the first adhesive composition 16. A uniform layer of powder of the hydrogel-forming composition 18 is desired with sufficient surface area exposed for hydration. Typically, an adhesive composition 16 layer in the thickness range from about 5 micrometers to about 150 micrometers is suitable. As illustrated, the device further comprises a substantially dry, second microbial growth nutrient 24 disposed on a portion of the first major surface 22a of the cover sheet 22. In such embodiments, the device typically further comprises a second adhesive composition 26 adhered to the second microbial growth nutrient composition. In some embodiments, the second microbial growth nutrient composition comprises a second microbial growth nutrient and at least one cold-water-soluble gelling agent. In some embodiments, the device further comprises a cold-water-soluble second hydrogel-forming composition 28 adhered to the second adhesive composition 26. A uniform layer of powder of the hydrogel-forming composition 28 is desired with sufficient surface area exposed for hydration. In alternate embodiments, the device further comprises a second adhesive composition 26 disposed on a portion of the first major surface 22a of the cover sheet 22. In some embodiments, the second adhesive composition also contains at least one indicator agent.

Figure 3:
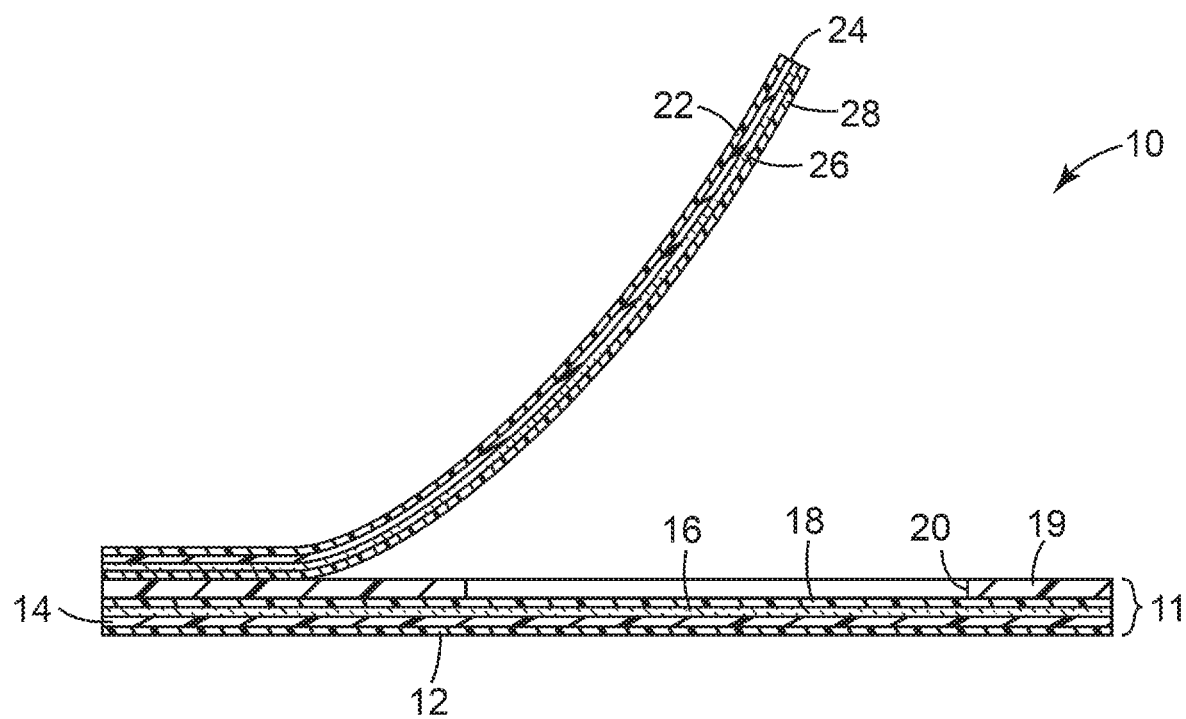
FIG. 3 is a cross sectional view of the device of FIG. 1, including an optional spacer.

Referring to FIG. 3, a cross sectional view is provided of the device 10 of FIG. 1, plus further including an optional spacer 19 disposed on the cold-water-soluble first hydrogel-forming composition 18. In general, the spacer 19 comprises a water-insoluble substrate defining an aperture 20, the spacer 19 being positioned between the substrate sheet 12 and the cover sheet 22. Typically, the aperture 20 defines a peripheral boundary of a sample-receiving zone. The aperture 20 can be any shape. Non-limiting examples of useful shapes for the aperture 20 include a square, a rectangle, a circle, an oval, a polygon, a hexagon, and an octagon. The area of the sample-receiving zone (and aperture 20) may be selected based on, for example, the volume of sample (e.g., aqueous liquid) to be deposited in the zone. In any embodiment, for a 0.5-3 milliliter sample, the area of the sample-receiving zone is about 10 cm$^2$ or about 15 cm$^2$. In any embodiment, for a 1-5 milliliter volume of sample, the area of the sample-receiving zone is about 20 cm$^2$, about 25 cm$^2$, about 30 cm$^2$, about 31 cm$^2$, or about 25-35 cm$^2$.

Suitable adhesives are transparent when wetted with water. As noted above, the adhesive composition is often water insoluble. In certain embodiments, the adhesive composition comprises a solvent based adhesive. The first adhesive composition and, if present, second adhesive composition often is a pressure sensitive adhesive. For instance, the adhesive may be a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer comprises a lower alkyl (C2 to C10) monomer of acrylic acid, including, for example, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl (C2 to C5))(meth)acrylamides, N-methyl(meth)acrylamide, N,N-dimethyl(meth) acrylamides, or mixtures thereof. Suitable adhesives may also include those described in U.S. Pat. Nos. 4,565,783, 5,089,413, 5,681,712, and 5,232,838. In some embodiments, silicone pressure sensitive adhesives may be used, including for example those described in U.S. Pat. Nos. 7,695,818 and 7,371,464.

In the present disclosure, the cover sheet 22 is usually selected to be transparent, in order to facilitate counting of microbial colonies, and is typically also selected to be impermeable to bacteria and have low moisture vapor transmission rate (i.e., the cover sheet 22 prevents undesired contamination of the dehydrated medium during shipping, storage and use of the devices and provides an environment which will support the growth of microorganisms during the incubation period). In some embodiments, the cover sheet 22 has the same properties (e.g., being water-proof) as the substrate 12. The cover sheet 22 can be selected to provide the amount of oxygen transmission necessary for the type of microorganism desired to be grown. For example, some polyester films have low oxygen permeability (less than 5 g/645 cm$^2$/24 hours per 25 micrometers of thickness) and would be suitable for growing anaerobic bacteria. On the other hand, some polyethylenes have high oxygen permeability (e.g., approximately 500 g/645 cm$^2$/24 hours per 25 micrometers of thickness) and would be suitable for aerobic organisms. Suitable material for the cover sheet 22 includes polypropylene, polyester, polyethylene, polystyrene, or silicone. In certain embodiments, the cover sheet 22 comprises oriented polypropylene, such as biaxially oriented polypropylene, which in some exemplary embodiments has a thickness of about 40 micrometers.

In any embodiment, the cover sheet 22 can be free of any coating, or can be coated, e.g., on the surface facing the dehydrated medium with a layer of pressure-sensitive adhesive, in order to facilitate sealing of the cover means over the medium. Furthermore, the cover sheet 22 can optionally be coated on the surface facing the first cold-water-soluble hydrogel-forming composition 18 with layers of an adhesive composition 26 and a second cold-water-soluble hydrogel-forming composition 28, that are the same as or different from the first adhesive composition 16 and the first cold-water-soluble hydrogel-forming composition 18, respectively. Coatings on the cover sheet 22 can cover the entire surface, but preferably cover at least the part of the surface that is intended to cover the growth region of the culture device. Such coated coversheets are particularly preferred when it is desired to provide a device with more gelling agent than can be incorporated in the first cold-water-soluble hydrogel-forming composition alone.

Figure 2:
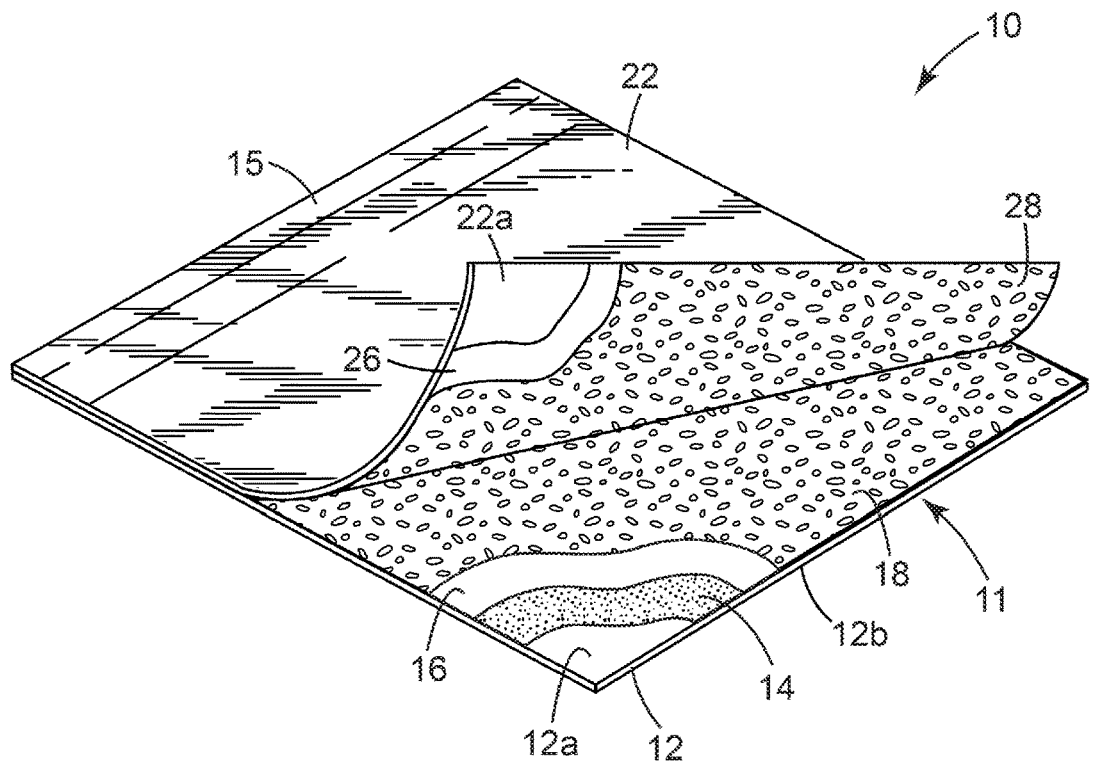
FIG. 2 is a top perspective view, partially in section, of another exemplary embodiment of a microbiological growing device.

Referring to FIG. 2, another exemplary embodiment of a device for growing microorganisms. The substrate 12 and layers disposed thereon are shown to be the same as illustrated in FIG. 1. In certain embodiments, the device 10 comprises a second adhesive composition 26 adhered to a portion of the first major surface 22a of the cover sheet 22. In some embodiments, the device further comprises a cold-water-soluble second hydrogel-forming composition 28 adhered to the second adhesive composition 26. A uniform layer of powder of the hydrogel-forming composition 28 is desired with sufficient surface area exposed for hydration. In some embodiments, the second adhesive composition also contains at least one indicator agent.

In any embodiment, each one or more layers of adhesive is water-insoluble and non-inhibitory to the growth of microorganisms, and are sufficiently transparent when wet to enable the viewing of gas bubbles or microbial colonies through the adhesive. In some embodiments, the layer of adhesive comprises a pressure-sensitive adhesive. For instance, the adhesive may be a pressure-sensitive adhesive such as a water-insoluble adhesive comprising a copolymer of an alkyl acrylate monomer. In certain embodiments, the adhesive composition comprises a solvent based adhesive.

In certain embodiments, the cold-water-soluble hydrogel-forming composition contains one or more organic cold-water-soluble agents, such as alginate, carboxymethyl cellulose, tara gum, hydroxyethyl cellulose, hydroxypropyl methylcellulose, guar gum, locust bean gum, xanthan gum, polyacrylamide, polyurethane, polyethylene oxides. Combinations of natural and/or synthetic gelling agents are contemplated. Preferred gelling agents include guar gum, xanthan gum, and locust bean gum, these gelling agents being useful individually or, in any embodiment, in combination with one another. A uniform monolayer of a cold-water-soluble hydrogel-forming composition is desired with sufficient surface area exposed for hydration. In any embodiment, the first and/or second cold-water-soluble hydrogel-forming composition comprises a mixture of gelling agents. Optionally, the powdered cold-water-soluble hydrogel-forming composition may further comprise an inducer, and indicator agent, or a combination of these.

Suitable microbial growth nutrient compositions typically comprise for instance and without limitation one or more nutrients including a meat peptone, a casein peptone, a gelatin peptone, a soy peptone, a beef extract, a yeast extract, lactose, glucose, dextrose, tryptose, galactose, tryptone, a fat, a mineral, or a vitamin. Further, non-limiting examples of nutrients, additional gelling agents, and mixtures thereof for supporting growth of microorganisms in a device of the present disclosure include those described in U.S. Pat. Nos. 4,565,783; 5,089,413; 5,232,838; 5,364,766; 5,443,963; 5,462,860; 5,601,998; 5,635,367; and 5,681,712; these references also include non-limiting examples of indicator agents (e.g., detection reagents) and inducers.

Suitable indicator agents can include one or more indicator agents for detecting an alkyl esterase activity, a phosphatase enzyme activity, a glycosidase enzyme activity, a peptidase enzyme activity, a pH change, or a redox change. In any embodiment, the one or more indicator agents may be dissolved in an organic solvent (e.g., methanol) and blended with an adhesive composition (e.g., the first adhesive composition 14 and/or the second adhesive composition 24)

before applying the composition to the substrate sheet 12 and/or cover sheet 22. In any embodiment, the first cold-water-soluble hydrogel-forming composition and/or the second cold-water-soluble hydrogel-forming composition may comprise one or more indicator agents, either the same or different.

Optionally, a plurality of indicator agents may be used for detecting a presence of an aerobic or aerotolerant bacterium. In any embodiment, suitable indicator agents comprise, for example, enzyme substrates. In any embodiment, each indicator agent can comprise a reporter group (e.g., a fluorogenic group or chromogenic group) that permits detection of a reaction between the indicator agent and a biological activity (i.e., an enzyme activity associated with an aerobic or aerotolerant bacterium) and the indicator agent. One suitable indicator agent is triphenyl tetrazolium chloride (TTC). Suitable redox indicators (e.g., triphenyl tetrazolium chloride) include a reporter group (e.g., a chromogenic and/or fluorogenic group) that is oxidized or reduced to form a detectable signal (e.g., a detectable color change or fluorescence change). For example, triphenyl tetrazolium chloride is reduced by bacteria to form a formazan product having a detectable color. Detecting the detectable reporter group (e.g., formazan) in a culture device of the present disclosure is indicative of a possible presence of an aerobic or aerotolerant bacterium.

Further, in a method wherein the culture medium comprises bromcresol purple as a pH indicator, the culture medium will have a purple or gray appearance at about a neutral pH. As the microorganisms grow and ferment a carbohydrate (e.g., glucose) in the culture medium, the bromcresol purple indicator will appear yellow adjacent the growing bacterial colonies. For example, in a method wherein the culture medium comprises chlorophenol red as a pH indicator, the culture medium will have a red or violet appearance at about a neutral pH. As the microorganisms and ferment a carbohydrate in the culture medium, the chlorophenol red indicator will appear yellow adjacent the growing microbial colonies. Gas bubbles, if present in the growth compartment and associated with a colony of microorganisms (e.g., either touching the colony or within a distance of about 1 mm or less from the colony), can be detected visually and/or by the use of an imaging system. The gas bubbles may be associated with a visible colony and/or an acid zone detectable by a change in the color of a pH indicator in a region adjacent the colony of microorganisms. The gas bubble may comprise carbon dioxide generated by anaerobic fermentation of a carbohydrate, for example.

In a further aspect, another device is provided. More particularly, a device is provided including a body member including a substrate having a first major surface and a second major surface and a cover sheet attached to the body member, where the cover sheet includes a first major surface facing the body member. The device further includes a substantially dry, first microbial growth nutrient composition disposed on a portion of the first major surface of the cover sheet, a first adhesive composition adhered to the first microbial growth nutrient composition, and a cold-water-soluble first hydrogel-forming composition adhered to the first adhesive composition. Preferably, the device also includes a spacer disposed on a first major surface of the body member. Optionally, one or more compositions (e.g., a second cold-water-soluble first hydrogel-forming composition, a second adhesive composition, and/or a second nutrient composition) are coated on the substrate, but often no coatings are provided on the substrate.

Figure 15:
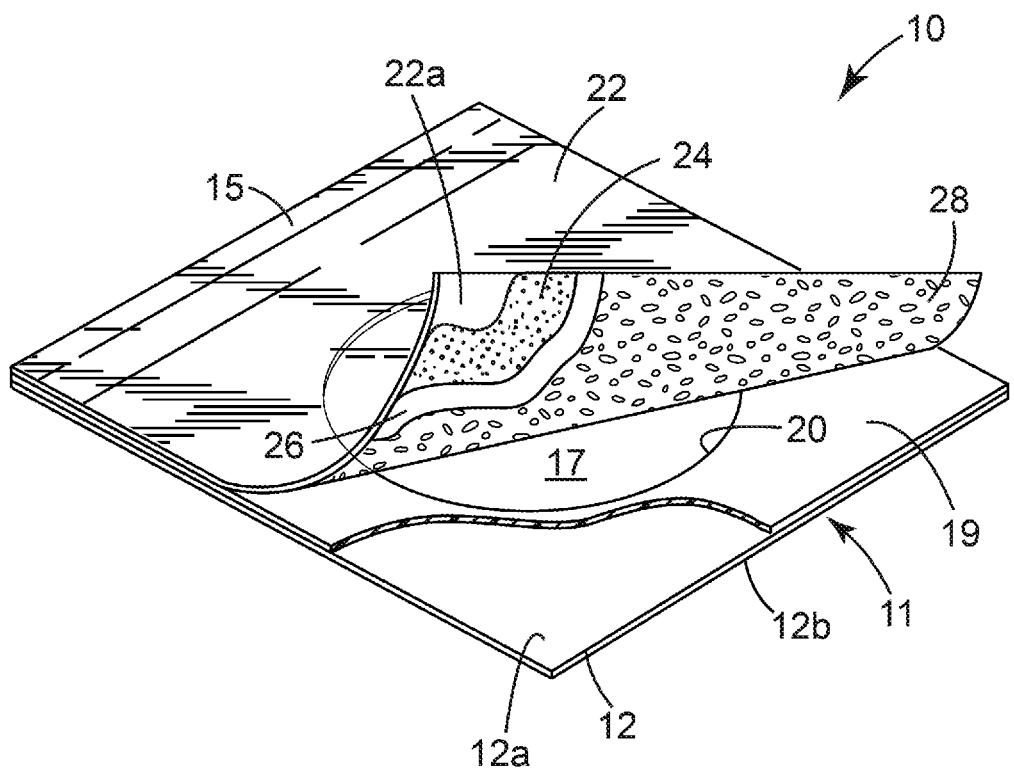
FIG. 15 is a top perspective view, partially in section, of yet another exemplary device according to the present disclosure.

More particularly, FIG. 15 illustrates an exemplary embodiment of a device for growing microorganisms. The device 10 includes a body member 11 including a substrate 12 having a first major surface 12a (e.g., upper surface) and a second major surface 12b (e.g., lower surface) and a cover sheet 22 attached to the body member 11, where the cover sheet 22 includes a first major surface 22a (e.g., upper surface) facing the body member 11. The device 10 further includes a substantially dry, first microbial growth nutrient composition 24 disposed on a portion of the first major surface 22a of the cover sheet 22, a first adhesive composition 26 adhered to the first microbial growth nutrient composition 24, and a cold-water-soluble first hydrogel-forming composition 28 adhered to the first adhesive composition 26. Preferably, the device also includes a spacer 19 disposed on the first major surface 12a of the substrate 12. In use, a user separates the cover sheet 22 from the substrate 12 sufficiently to add an amount of a sample containing at least one microorganism within an aperture 20 defined by the spacer 19, places the cover sheet 22 back in contact with the substrate 12 to form an inoculated device, and incubates the inoculated device. The area on the first major surface 12a of the substrate 12 defined by the aperture 20 may also be referred to as a sample-receiving zone 17. All of the materials and compositions discussed in detail above with respect to the first aspect may be used in this device.

In a second aspect, another microbial detection device is provided. The microbial detection device includes a water-proof pouch including a first wall portion having an inner surface and an outer surface, a second wall portion having an inner surface and an outer surface, and a porous membrane filter disposed in the pouch between the inner surface of the first wall portion and the inner surface of the second wall portion. The membrane filter has a first major surface and a second major surface opposite the first major surface. The water-proof pouch further includes a first compartment defined in part by the inner surface of the first wall portion and defined in part by the first major surface of the membrane filter and a sealable sample port that provides access to deposit a liquid into the first compartment. Additionally, the water-proof pouch includes a second compartment defined in part by the inner surface of the second wall portion and defined in part by the second major surface of the membrane filter, and an absorbent pad disposed in the second compartment. The membrane filter permits passage of aqueous liquids from the first compartment to the second compartment and prevents passage of particles of a predetermined size from the first compartment to the second compartment. The water-proof pouch also includes a substantially dry microbial growth nutrient composition disposed on a portion of the pouch in the first compartment, an adhesive composition adhered to the microbial growth nutrient composition, and a cold-water-soluble hydrogel-forming composition adhered to the adhesive composition.

For instance, a microbial detection device can comprise:
a water-proof pouch comprising:
a first wall portion having an inner surface and an outer surface;
a second wall portion having an inner surface and an outer surface;
a porous membrane filter disposed in the pouch between the inner surface of the first wall portion and the inner surface of the second wall portion, the membrane filter having a first major surface and a second major surface opposite the first major surface;

a first compartment defined in part by the inner surface of the first wall portion and defined in part by the first major surface of the membrane filter;

a sealable sample port that provides access to deposit a liquid into the first compartment;

a second compartment defined in part by the inner surface of the second wall portion and defined in part by the second major surface of the membrane filter;

wherein the membrane filter permits passage of aqueous liquids from the first compartment to the second compartment and prevents passage of particles of a predetermined size from the first compartment to the second compartment;

a substantially dry microbial growth nutrient composition disposed on a portion of the pouch in the first compartment;

an adhesive composition adhered to the microbial growth nutrient composition;

a cold-water-soluble hydrogel-forming composition adhered to the adhesive composition; and an absorbent pad disposed in the second compartment.

Regarding the microbial detection device of the second aspect, FIGS. 5-8 show various views of one embodiment of a device 500 according to at least one embodiment of the present disclosure. The device 500 comprises a waterproof pouch 55 defined by at least one wall. The at least one wall comprises a first wall portion 510 and a second wall portion 520. The first wall portion 510 has an inner surface 512 and an outer surface 514. The second wall portion 520 has an inner surface 522 and an outer surface 524. Disposed in the pouch 55 between the inner surface 512 of the first wall portion 510 and the inner surface 522 of the second wall portion 520 is a membrane filter 540. The membrane filter has a first major surface 542 and a second major surface 544 opposite the first major surface.

Figure 9:
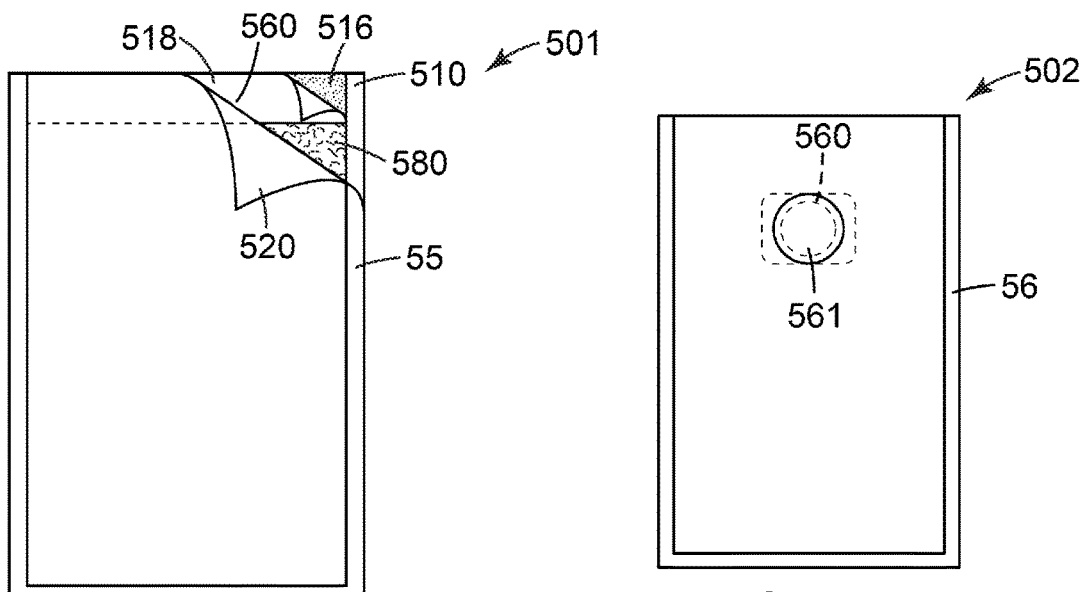
FIG. 9 is a plan view, partially in section, of an alternative embodiment of the device of FIG. 5, showing an adhesive strip and a release liner releasably adhered thereto that form a sealable sample port.

Although the first wall portion 510 and second wall portion 520 may be distinct portions of a unitary pouch or bag, in any embodiment, the first wall portion and second wall portion alternatively may consist of separate sheets of polymeric film that are joined together (e.g., heat-sealed and/or adhesively sealed along the edges) to form the pouch, as shown in FIG. 9, for example, and described herein.

The pouch 55 is divided into at least two compartments (first compartment 550 and second compartment 552, respectively). The first compartment 550 is defined in part by the inner surface 512 of the first wall portion 510 and also defined in part by the first major surface 542 of the membrane filter 540. The first compartment 550 has a sealable sample port 560. In the illustrated embodiment of FIGS. 5-7, the sealable sample port 560 is simply an opening 561 along a portion of the perimeter of the pouch 55. Nonlimiting exemplary means for closing the opening 561 are discussed herein. The second compartment 552 is defined in part by the inner surface 522 of the second wall portion 520 and defined in part by the second major surface 544 of the membrane filter 540.

The first compartment 550 is configured to receive a volume of liquid sample to be tested for presence of target microorganisms. The volume of liquid the first compartment 550 can receive will be influenced by several features of the device including, for example, the dimensions (e.g., the length "L" and width "W" shown in FIG. 7) of the first compartment and the flexibility of the materials (e.g., the first wall portion 510 and the membrane filter 540) that define the first compartment. The second compartment 552 is configured to receive a volume of liquid approximately equal to the volume of liquid sample to be tested. Thus, the pouch of a device of the present disclosure may be dimensioned to hold up to about twice the volume of the sample to be tested.

In any embodiment, a device of the present disclosure is configured to test (i.e., configured to receive) at least about 25 milliliters of liquid sample. In any embodiment, a device of the present disclosure is configured to test at least about 50 milliliters of liquid sample. In any embodiment, a device of the present disclosure is configured to test at least about 75 milliliters of liquid sample. In any embodiment, a device of the present disclosure is configured to test at least about 100 milliliters of liquid sample. In any embodiment, a device of the present disclosure is configured to test at least about 125 milliliters of liquid sample. In any embodiment, a device of the present disclosure is configured to test at least about 150 milliliters of liquid sample. Thus, in any embodiment, the device according to the present disclosure is configured to receive at least about 25 mL, at least about 50 mL, at least about 75 mL, at least about 100 mL, at least about 125 mL, at least about 150 mL of liquid sample (e.g., aqueous liquid sample). Accordingly, in any embodiment, the first compartment of the device is configured to receive at least about 25 mL, at least about 50 mL, at least about 75 mL, at least about 100 mL, at least about 125 mL, at least about 150 mL of liquid sample (e.g., aqueous liquid sample).

The pouch 55 further comprises a substantially dry microbial growth nutrient composition disposed on a portion of the pouch (e.g., the first wall portion 510 of the pouch) in the first compartment 550. In some embodiments, the microbial growth nutrient composition comprises a microbial growth nutrient and at least one cold-water-soluble gelling agent. The pouch 55 additionally comprises an adhesive composition adhered to the microbial growth nutrient composition. In any embodiment, the adhesive composition comprises a pressure sensitive adhesive. As discussed above with respect to the first embodiment, the adhesive composition is often water insoluble. In certain embodiments, the adhesive composition comprises a solvent based adhesive. For instance, the adhesive may be a pressure-sensitive adhesive such as a water-insoluble adhesive comprising a copolymer of an alkyl acrylate monomer and an alkyl amide monomer.

In any embodiment, a device of the present disclosure comprises an effective amount of one or more dry nutrients (e.g., a nutrient medium selected to support growth of the target microorganism). The microbial growth nutrient composition typically comprises at least one nutrient selected from the group consisting of a meat peptone, a casein peptone, a gelatin peptone, a soy peptone, a beef extract, a yeast extract, lactose, glucose, dextrose, tryptose, galactose, tryptone, a fat, a mineral, or a vitamin.

Similar to the devices according to the first aspect, it has been unexpectedly discovered that despite the lack of compatibility between the materials of the microbial growth nutrient composition (e.g., being water soluble) and the adhesive composition (e.g., being water insoluble), a sufficient amount of nutrients are able to traverse through the layer of the adhesive composition to be available for microorganism consumption in the devices according to the second aspect. Moreover, due to being covered (e.g., masked) by the first adhesive composition, the nutrients are not exposed on the surface of the film and thus are protected from washing off when a fluid sample is introduced into the device. This is particularly relevant for applications in which the sample must contact the powder layer and then pass through a filter (such as devices according to this second aspect).

Figure 6:
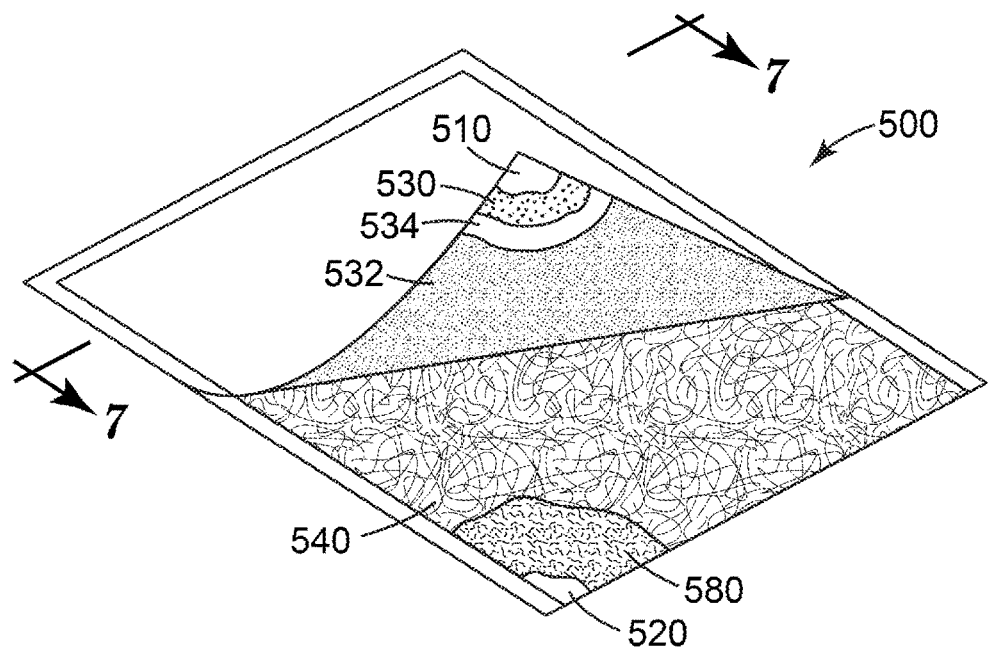
FIG. 6 is another perspective view, partially in section, of the device of FIG. 5.
Figure 7:
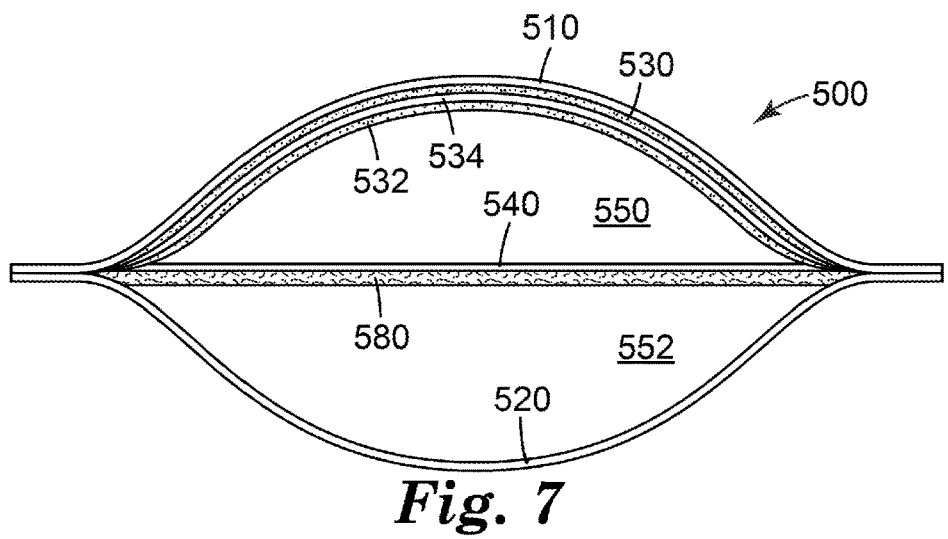
FIG. 7 is a cross-sectional view, taken along the line 7-7, of the device of FIG. 6.
Figure 8:
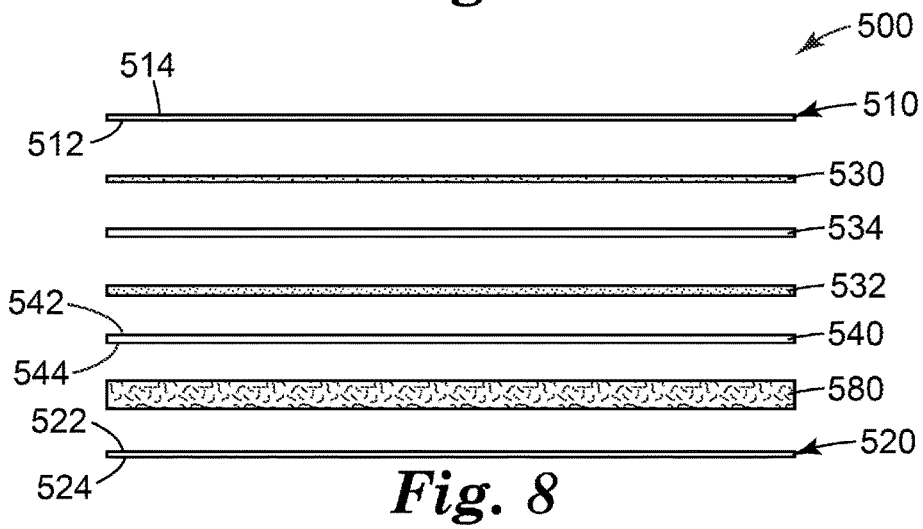
FIG. 8 is an exploded cross-sectional view, of the device of FIG. 6.
Figure 11:
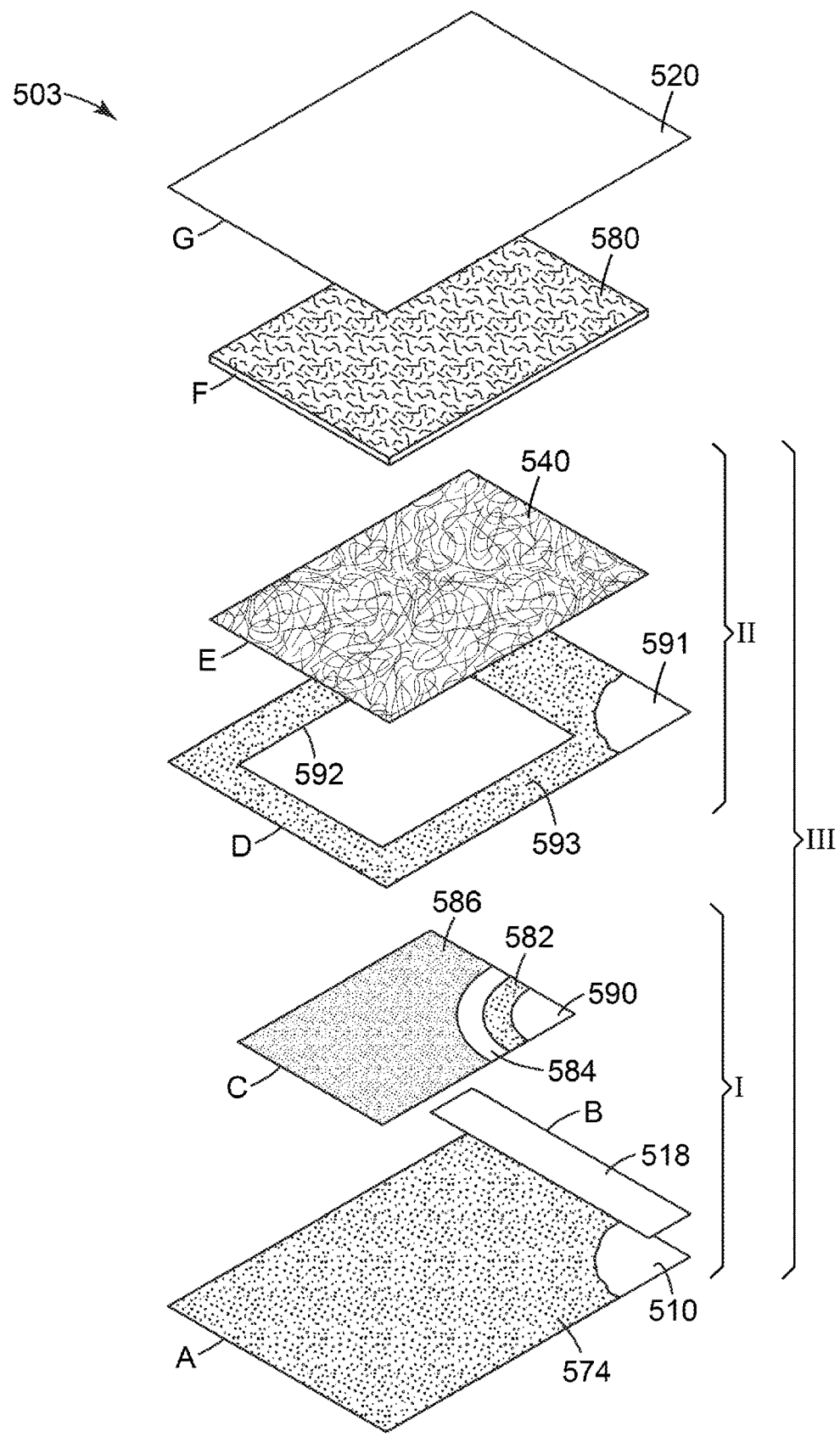
FIG. 11 is an exploded view of another alternative embodiment of a device according to the present disclosure.

Further, a dry (i.e., substantially water-free) cold-water-soluble hydrogel-forming composition is adhered to the adhesive composition. For instance, FIGS. 6 and 7 show the cold-water-soluble hydrogel-forming composition as a dry coating 532 disposed on the layer of adhesive composition 534, which is adhered to the layer of microbial nutrient composition 530, which is disposed on the inner surface 512 of the first wall portion 510. In addition, the pouch 55 has an absorbent pad 580 disposed in the second compartment 552. In any embodiment, the dry coating 532 may be adhered to a first substrate (e.g., adhered to an adhesive layer coated on the substrate) that is adhered to the first wall portion 510 of the pouch 55. This optional configuration is shown in FIG. 11 and described herein below.

Whether the cold-water-soluble hydrogel-forming composition is adhered to the first wall portion of the pouch or to a first substrate that is adhered to the first wall portion, the area defined by the coating comprising the cold-water-soluble hydrogel-forming composition also defines the area in which microorganisms from the sample grow and are enumerated after a sample is deposited into the first compartment. Because the device comprises an absorbent pad (described below) that absorbs most of the liquid from the sample, the cold-water-soluble hydrogel-forming composition is hydrated by only a fraction of the liquid sample. Advantageously, these devices use a surprisingly smaller ratio of growth area: sample volume than previously-reported thin-film culture devices. For example, a device according to the second aspect of the present disclosure is configured to receive 100-150 mL of a liquid sample and has a growth area (that includes a cold-water-soluble hydrogel-forming composition) of about 80 cm$^2$. Thus, the microorganisms from the 150 mL sample volume is spread over a growth area that is equivalent to less than 1 cm$^2$ per mL of sample.

The pouch 55 (i.e., at least one wall, and wall portions thereof) is fabricated of a water-proof, deformable material. In any embodiment, the deformable material may comprise a flexible, sheet-like material such as a polymeric film, for example. Suitable materials for use when fabricating the at least one wall include polyethylene, polypropylene, polyethylene terephthalate, polyamide, polyurethane, polyvinyl chloride, polyacrylate, polyurea, and combinations thereof. The at least one wall of the pouch can be relatively thin (e.g., approximately 25 microns thick) or relatively thicker (e.g., approximately 125 microns thick), provided at least a portion of the at least one wall (e.g., first wall portion 510, which is opposite the membrane filter 540 in the first compartment 550) can deform when the pouch 55 receives a liquid sample (not shown) and/or at least a portion of the at least one wall (e.g., second wall portion 520, which is proximate the absorbent pad described herein) can deform when at least a portion of the sample passes from the first compartment into the second compartment.

The membrane filter 540 permits passage of a liquid (an aqueous liquid, not shown) from the first compartment 550 to the second compartment 552 and prevents passage of particles of a predetermined size from the first compartment to the second compartment. Thus, when an aqueous liquid sample suspected of containing a target microorganism is placed into the first compartment 550, a first portion of the aqueous liquid passes (e.g., by gravity flow) through the membrane filter 540 into the second compartment 552 where it is absorbed by the absorbent pad 580. The target microorganism is trapped on or in the filter membrane 540 or is retained in a second portion of the aqueous liquid that remains in the first compartment 550.

The use of membrane filters to trap and retain microorganisms is well known in the art. Accordingly, there are a number of suitable membrane filters that can be used in a device according to the present disclosure. Nonlimiting examples of suitable membrane filters include fibrous membrane filters made of nylon, polyether sulfone, polytetrafluoroethylene, or cellulosic materials (e.g., mixed cellulose esters), microporous plastic films (e.g., laser-etched polycarbonate film), and ceramic membrane filters.

The porosity of the membrane filter generally is chosen so that the target microorganisms will not pass all the way though the pores from one side of the membrane filter to the other side, thereby insuring that substantially all target microorganisms in the sample are retained by the filter. Typical bacteria are about 0.5 to 5.0 μm in length. Certain smaller bacteria, such as *Mycoplasma* spp., are approximately 0.3 μm in diameter. Yeast cells are generally larger than bacteria. Typical yeast cells are approximately 3-4 μm in diameter, although some are as large as about 40 μm in diameter. Molds may exist as single cells, spores, or filamentous hyphae. Although typically larger than bacteria, the average size of mold cells varies by species. Accordingly, the selection of a membrane filter with a suitable pore size may depend upon the target microorganism. For example, a membrane filter with a nominal pore size of 1.0 μm or less, 0.8 μm or less, 0.6 μm or less, 0.4 μm or less, 0.2 μm or less, 0.1 μm or less, 0.05 μm or less, 0.03 μm or less, 0.02 μm or less, or 0.01 μm or less may be suitable to capture and detect target bacteria. For capturing and detecting target yeast or mold microorganisms, a membrane filter with a nominal pore size of 12 μm or less, 8 μm or less, 5 μm or less, 3 μm or less, 2 μm or less, 1 μm or less, 0.8 μm or less, 0.6 μm or less, 0.4 μm or less, 0.2 μm or less, or 0.1 μm or less may be suitable.

Membrane filters may be prepared manually from suitable filtration media or, alternatively, may be purchased in pre-cut sizes and shapes. The size and shape of the membrane filter can be chosen based upon the sample volume and the expected load of particulate material in the sample. In general, membrane filters with larger surface areas will allow for higher filtration rates than membrane filters with smaller surface areas. Membrane filters may be used in combination with other filtration media (e.g., a prefilter, to trap larger debris in the sample) or other membrane filters.

In any embodiment, the membrane filter may be supported (e.g., by a scrim, not shown) to provide physical stability for the membrane during use. In any embodiment, the support may be attached to the membrane filter (e.g., on the second major surface). In any embodiment, the membrane filter can comprise a wetting agent (e.g., a nonionic surfactant) to facilitate rapid and complete penetration of the liquid sample throughout the membrane filter. Preferably, the wetting agent is in an amount sufficient to facilitate wetting the membrane with an aqueous liquid, but in an amount that does not substantially inhibit growth of the target microorganism when using the device.

The dry, cold-water-soluble hydrogel-forming composition is hydrated and forms a hydrogel when an aqueous sample is placed into the first compartment 550 of the pouch 55. As the first portion of the aqueous liquid moves through the membrane filter 540 from the first compartment 550 to the second compartment 552, the hydrogel contacts the first surface of the membrane filter 540, thereby immobilizing any microorganisms retained on or in the membrane filter.

Cold-water-soluble gelling agents that are suitable for use in thin-film culture devices are known in the art and include, for example, cold-water-soluble natural and synthetic gelling agents. Natural gelling agents such as alginate, carboxymethyl cellulose, tara gum, hydroxyethyl cellulose, guar gum, locust bean gum, xanthan gum, and synthetic gelling agents such as polyacrylamide, polyurethane, polyethylene oxides, and mixtures thereof are generally suitable. Appropriate gelling agents can be selected according to the teaching of this disclosure and the disclosures of U.S. Pat. Nos. 4,565,783; 5,089,413; and 5,232,838. Other preferred gelling agents include hydroxypropyl methylcellulose; these gelling agents being useful individually, or preferably, in combination with another gelling agent such as one of the aforementioned gelling agents.

In any embodiment, the dry, cold-water-soluble hydrogel-forming composition can be disposed in the pouch as a dry powder adhered to an adhesive layer, as described herein. Processes and adhesives for coating a dry powder onto a flexible film for use in a thin-film culture device are described, for example, in U.S. Pat. Nos. 4,565,783; 5,089,413; and 5,232,838. In any embodiment, the adhesive layer, if present may comprise an indicator for indicating microorganism growth. For example, the adhesive may comprise triphenyltetrazolium chloride as described in U.S. Pat. No. 5,409,838, which is incorporated herein by reference in its entirety.

In any embodiment, the dry, cold-water-soluble hydrogel-forming composition can be deposited onto the first wall portion of the pouch as an aqueous composition and subsequently dried, as described in U.S. Pat. Nos. 4,565,783; 5,089,413; and 5,232,838. Optionally, in any embodiment, the dried coating can be adhered to an adhesive layer coated onto the first wall portion of the pouch. In any embodiment, the adhesive layer may further comprise an indicator for indicating microorganism growth, as described above.

Before a liquid sample is deposited into the pouch, the absorbent pad 580 is preferably relatively thin (e.g., less than or equal to 5 mm thick, less than or equal to 4 mm thick, less than or equal to 3 mm thick, less than or equal to 2 mm thick, less than or equal to about 1 mm thick) and is configured to absorb a quantity of deionized water equal to many time its own weight (e.g., at least 100-times its own weight, at least 150-times its own weight, at least 200-times its own weight, at least 250-times its own weight, at least 300-times its own weight, at least 350-times its own weight, at least 400-times its own weight, at least 500-times its own weight). In any embodiment, the absorbent pad may comprise a plurality of materials such as, for example, a super-absorbent material (e.g., a superabsorbent polymer; "herein, "SAP") and a less-absorbent or nonabsorbent carrier (e.g., cellulosic fibers). A nonlimiting example of a suitable absorbent pad is a composite polyacrylate laminate structure comprising a superabsorbent polymer granule base disposed between two cellulose sheets. In any embodiment of the absorbent pad, the pad may comprise SAP granules disposed in an air-laid nonwoven material or SAP fibers blended with carrier fibers into a nonwoven material.

Optionally, in any embodiment (not shown), the absorbent pad may be coupled to a component of the pouch (e.g., the second wall portion) in the second compartment. Advantageously, this can keep the pad from deforming (e.g., as it swells with liquid migrating from the first compartment) to an extent that it loses contact with a substantial portion of the membrane filter. The pad may be coupled to the pouch via an adhesive (e.g., a pressure-sensitive adhesive), a thermal weld or other suitable attachment means known in the art. In any embodiment, the absorbent pad may be releasably coupled to the pouch (e.g., by a water-soluble gum). This embodiment hold the pad in a proper position to receive liquid passing through the membrane filter, but permits lateral movement of the pad as it swells due to absorption of a large quantity of the liquid.

Referring back to the drawings, FIG. 9 shows one embodiment of a sealable sample port 560 of a device 501 according to the present disclosure. The device 501 comprises a pouch 55 having a first wall portion 510, a second wall portion 520, and a sealable sample port 560 consisting of an opening, each as described herein. The inner surface 512 of the first wall portion 510 comprises an adhesive strip 516 coated thereon along the edge of the inner surface proximate the opening. Adhered to the adhesive strip 516 is a release liner 518. After the sample is deposited (e.g., by pouring or pipetting) into the first compartment (not shown in FIG. 9) through the opening (sample port 560), the operator removes the release liner and contacts the adhesive strip 516 with the inner surface 522 of the second wall portion 520 proximate the opening in order to seal the opening. Optionally, the operator can expel (out of the opening) some or all of the air from the first compartment 550 when completing the sealing process.

Figure 10:
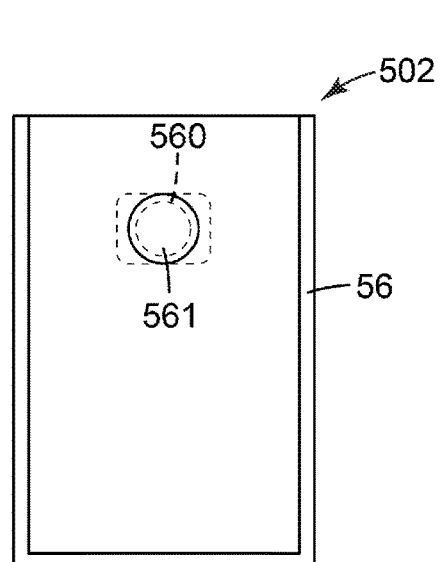
FIG. 10 is a plan view of an alternative embodiment of a device according to the present disclosure, wherein the device comprises a sealable sample port with a screwcap.

FIG. 10 shows an alternative embodiment of a device 502 comprising a pouch 56 comprising a sealable sample port 560 with an opening 561. In this embodiment, the sealable sample port 560 is a screw-cap opening into which the liquid test sample can be poured or pipetted, for example. Alternatively, in any embodiment, the sealable sample port 560 can be a pierceable, elastically-deformable septum through which a needle or a pipet tip can be introduced to deliver the sample into the first compartment. After the needle or pipet is withdrawn from the septum, the elastically-deformable septum reseals the port. Advantageously, in these embodiments, the introduction of air into the first compartment can be minimized.

In another alternative embodiment (not shown), the sealable sample port can comprise interlocking zipper components (e.g., similar to a ZIPLOK plastic storage bag) on each of the first wall portion and second wall portion and a zipper component that is used cooperatively with the interlocking components to open or seal the first compartment.

In another aspect, the present disclosure provides a method of assembling a large-volume, thin-film culture device. Devices of the present disclosure can be assembled entirely from sheet-like materials. Advantageously, this enables the use of roll-to-roll processes when assembling a plurality of devices. FIGS. 11-14 show various views of an alternative embodiment of a device 503 according to the present disclosure.

FIG. 11 shows the sheet-like materials that are used to assemble one embodiment of a device according to the present disclosure. Each part of the device can be cut into appropriately-sized sheets and subsequently assembled into the device or, alternatively can be cut to the appropriate size using controlled-depth die cutting using a roll-to-roll process known in the art.

Figure 12A:
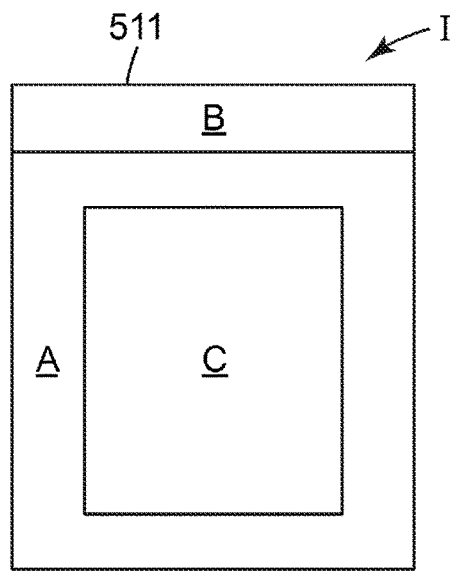
FIG. 12A is a first subassembly of the device of FIG. 11.

In any embodiment, a device of the present disclosure can be partially assembled into one or more subassembly, which is subsequently combined with other components to make the device. Referring to FIG. 11, the device 503 includes a first subassembly I that comprises a first part A, a second part B, and a third part C. Another view of the assembled first subassembly I is shown in FIG. 12A. The first part A consists of the first wall portion 510 with an adhesive layer 574 coated thereon as described herein. Second part B consists of a release liner 518 as described herein. Third part C consists of a first substrate 590 coated on one side with a substantially dry microbial growth nutrient composition 582. Adhered to the microbial growth nutrient composition 582 is an adhesive layer 584. Disposed on the adhesive layer 584 is a coating 586 that comprises the dry, cold-water-soluble hydrogel-forming composition described herein. The coating 586 can be deposited onto the adhesive layer 586 as a dry powder or as a liquid composition that is subsequently dried to a substantially water-free state, as described hereinabove. The first substrate 590 can comprise a sheet-like material similar to those used for the walls of the pouch as described above. Alternatively, the first substrate can comprise a nonwoven fabric or a cellulosic material (e.g., paper). In any embodiment, the cellulosic material can be coated with a waterproof coating that is substantially noninhibitory to growth of microorganisms. The area defined by the coating 584 on third part C also defines the growth and colony-enumeration area in the assembled device.

When assembling subassembly I, the release liner 518 is releasably adhered to the adhesive layer 574 along the edge (edge 511) of the first wall portion 510 that forms the opening of the assembled device. In addition, the third part C is positioned centrally over part A with the coating 586 facing away from the adhesive layer 574. Part C is then contacted with adhesive 574 to affix part C to part A with the coating 586 exposed., as shown in FIG. 12A.

Referring back to FIG. 11, a second subassembly II includes a fourth part D and a fifth part E. The fourth part D comprises a second substrate 591. The second substrate 591 forms a frame comprising an aperture 592. The second substrate 591 is coated on one side with an adhesive layer 593. The second substrate 591 can comprise a sheet-like material (e.g., a flexible film) similar to those used for the walls of the pouch as described above. Alternatively, the second substrate can comprise a nonwoven fabric or a cellulosic material (e.g., paper). In any embodiment, the cellulosic material can be coated with a waterproof coating that is substantially noninhibitory to growth of microorganisms. Optionally, the absorbent pad can be coupled to the second substrate in the second compartment.

Figure 12B:
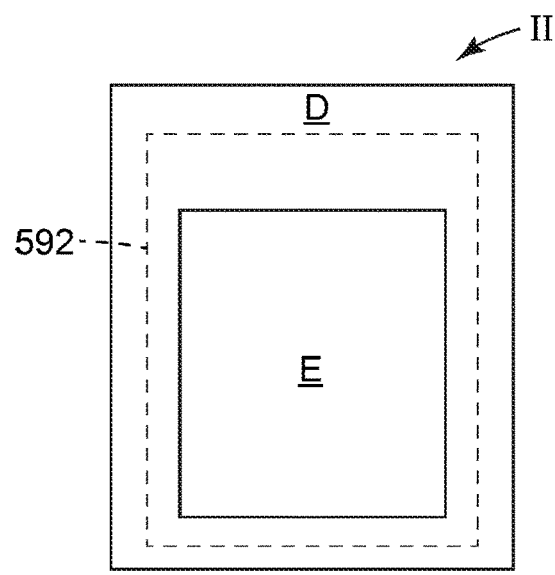
FIG. 12B is a second subassembly of the device of FIG. 11.

The second subassembly II also includes the fifth part E (i.e., membrane filter 540, as described herein). The membrane filter 540 is dimensioned so that it completely covers the area defined by the aperture 592. When assembling subassembly II, the membrane filter 540 is adhered to the adhesive layer 593 so that it completely covers the aperture 592 of the second substrate 591, as shown in FIG. 12B. In use, liquid passes through the aperture from the first compartment to the second compartment of the device as the liquid passes through the membrane filter. In any embodiment, the aperture 592 defines a first area and the coating 584 defines a second area. Preferably, the second area is greater than or equal to the first area. More preferably, the second area is shaped and dimensioned to completely overlap the area of the aperture.

Optionally, when assembling the device 503 of FIG. 11, the subassembly I can be coupled to subassembly II to form a subassembly III. This can be done by placing the back side (i.e., the side that does not include adhesive layer 593) of subassembly II in overlaying contact with the adhesive-coated side of subassembly I. In addition, the aperture 592 of subassembly II is aligned with subassembly I so that it overlaps the third part C of subassembly I.

Figure 13:
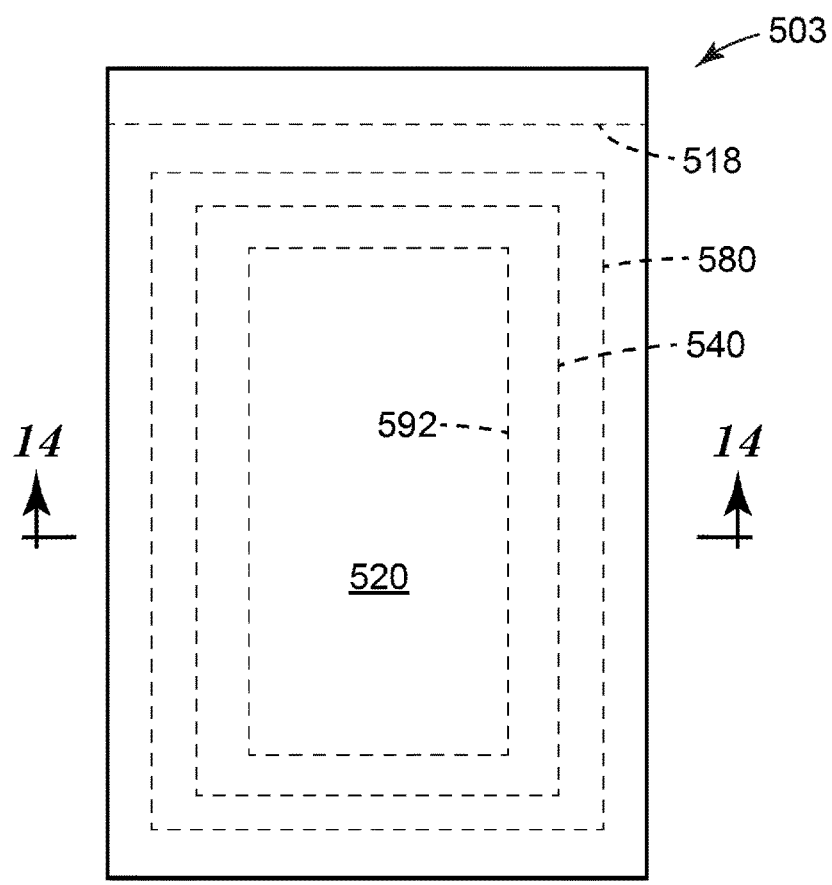
FIG. 13 is a plan view of the assembled device of FIG. 11.
Figure 14:
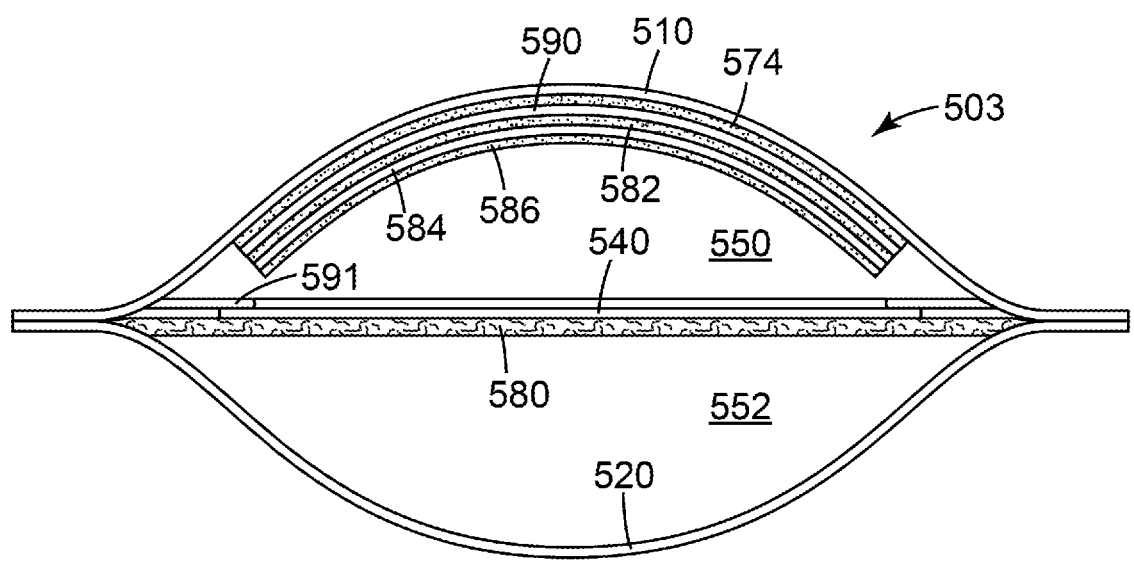
FIG. 14 is a cross-sectional view, taken along the line 14-14, of the device of FIG. 13.

To complete the construction of the device 503, the sixth part F (i.e., absorbent pad 580, as described herein) is placed in overlaying contact with the membrane filter 540 of the subassembly III and the seventh part (i.e., second wall portion 520, as described herein) is placed in overlaying contact with the first part A such that the seventh part G is adhesively coupled to the portion of the adhesive layer 574 at the periphery of the first part A. FIG. 13 shows a plan view and FIG. 14 shows a cross-sectional view of the assembled device 503 of FIG. 11.

In any embodiment, a device of the present disclosure further comprises an indicator reagent for indicating a presence of a viable microorganism. The indicator reagent is disposed in the pouch. In any embodiment, the indicator reagent may be disposed as a dry powder or dried coating in the first compartment and/or the second compartment of the pouch. In any embodiment, the indicator reagent can be disposed in an adhesive layer as described herein. Alternatively, or additionally, the indicator reagent may be a dry reagent coated onto an adhesive layer (e.g., with the cold-water-soluble hydrogel-forming composition as described herein).

In any embodiment, the indicator reagent may be a general indicator (e.g., a redox indicator such as triphenyltetrazolium chloride, for example) of viable microorganisms or an indicator of a large class of target microorganisms (e.g., total aerobic microorganisms). Alternatively, the indicator reagent can be an indicator (e.g., a chromogenic or fluorogenic enzyme substrate) that reacts with a smaller group of target microorganisms. A person having ordinary skill in the will recognize an appropriate indicator reagent for a particular target microorganism.

In any embodiment of a device according to the present disclosure, the device further comprises a stand-off layer (not shown) disposed in the second compartment between the membrane filter and the absorbent pad. The stand-off layer is a relatively-thin (e.g., about 0.1 mm to 2 mm thick) sheet-like material. In any embodiment, the stand-off layer is shaped and dimensioned to be at least coextensive with the membrane filter. In any embodiment, the stand-off layer is substantially less absorbent than the absorbent pad. In any embodiment, the absorbency of the stand-off layer is less than or equal to the absorbency of the membrane filter. The stand-off layer may comprise or consist essentially of a hydrophobic material (e.g., unmodified polypropylene).

The stand-off layer functions to permit the passage of aqueous liquid from the membrane filter to the absorbent layer during the initial period in which over half of the aqueous liquid deposited into the first compartment passes into the second compartment, while restricting diffusion of nutrient from the first compartment to the second compartment while the device is being incubated to facilitate microbial colony growth.

Suitable materials for use as the stand-off layer include, for example nonwoven fabrics comprising polypropylene; polyethylene; polyethylene terephthalate; a blend of polyethylene terephthalate and cellulose; a blend of polyethylene terephthalate and rayon; and mixtures thereof. Advantageously, devices comprising the stand-off layer can include dry nutrients coated on the first wall portion of the pouch and can retain enough nutrients in the hydrated cold water-soluble gelling agent to support growth of the target microorganisms in the hydrated nutrient gel.

In a third aspect, a method of detecting and enumerating at least one microorganism in a sample is provided. The method includes providing a device according to the first aspect, separating the first layer from the second layer, adding a predetermined volume of a sample containing at least one microorganism onto the first hydrogel-forming composition to form an inoculated device, contacting the first layer back to the second layer, incubating the inoculated device, and detecting the presence or an absence of a colony of the target microorganism in the device. Any of the devices described in detail above with respect to the first aspect are suitable for use in the methods of the third aspect.

For instance, the use of the devices of the present invention for detecting and enumerating microorganisms can be discussed with specific reference to the device of FIGS. 1 and 3. In certain embodiments, the second layer 22 acts as a cover sheet and is pulled back, and then a predetermined quantity of water or an aqueous test sample is placed on the first layer 12 of the body member 11. The particles of the gelling agent 16 adhered to the first layer 12 by the adhesive 14 are quickly hydrated or dissolved and a gel is formed. The second layer 22 is then replaced over the first layer 12 carefully, in order to minimize entrapment of air bubbles. The device is then incubated for a predetermined period of time. The inoculated device typically includes incubating for up to about 48 hours, or up to about 24 hours, or even up to about 14 hours. Any bacterial colonies growing in the medium can be detected and optionally enumerated (e.g., counted) through the transparent cover film. In some embodiments, the microorganisms can be counted using an automated system, such as an automated colony counter.

In a fourth aspect another method of detecting and enumerating at least one microorganism in a sample is provided. The method includes providing a device according to the second aspect, placing a predetermined volume of aqueous sample into the first compartment of the device, sealing the sample port, incubating the device, and detecting the presence or an absence of a colony of the target microorganism in the device. Any of the devices described in detail above with respect to the second aspect are suitable for use in the methods of the fourth aspect.

The method of the fourth aspect comprises a step of placing a predetermined volume of aqueous sample into the first compartment of the device of any one of the embodiments of the present disclosure. The aqueous sample can be any filterable liquid sample to be tested for presence of a target microorganism. The method is particularly useful for water samples that are suspected of containing relatively low concentrations (e.g., less than or equal to 10 microorganisms per milliliter, less than or equal to 1 microorganism per milliliter, less than or equal to 0.1 microorganisms per milliliter, less than or equal to 0.01 microorganism per milliliter,) of target microorganisms. Placing a predetermined volume of aqueous sample into the first compartment of the device comprises placing the predetermined volume into the device (e.g., via pipetting, pouring, injecting, or the like) through the sealable sample port.

The method further comprises a step of sealing the sample port. The procedure for sealing the sample port will depend upon the particular sealable sample port that is present in the device used in the method. For example, if the device 503 of FIGS. 11-13 is used in the method, sealing the sample port comprises removing the release liner 518 to expose an adhesive disposed on the first wall portion 510 and then contacting the adhesive on the first wall portion with the second wall portion to form a waterproof seal that closes the opening of the pouch.

For example, if the device 502 of FIG. 10 is used in the method, sealing the sample port comprises screwing the cap back onto the sample port, thereby forming a waterproof seal.

For example, if a device comprising an elastically-deformable pierceable septum (not shown) is used in the method, sealing the sample port will spontaneously occur as the pipet or needle used to introduce the sample into the device is withdrawn from the septum.

In any embodiment of the method, air may be expelled (e.g., manually, by squeezing) from the pouch via the sealable sample port before and or during the process of forming the waterproof seal.

The method further comprises a step of incubating the device for a period of time at a temperature that facilitates growth and detection of a target microorganism. A person having ordinary skill in the art will recognize the incubation temperature and period of time will depend upon a number of factors (e.g., the target microorganism, nutrients present in the sample, nutrients present in the device, inhibitory agents present in the sample and/or the device) and will adjust the incubation time and temperature accordingly.

The method further comprises a step of detecting a presence or an absence of a colony of the target microorganism in the device. In any embodiment, detecting a presence or an absence of a colony of the target microorganism in the device can comprise detecting a colony (e.g., visually or using machine vision) in the first compartment of the device. In any embodiment, detecting a presence or an absence of a colony of the target microorganism in the device can comprise detecting a change associated with the indicator reagent. The indicator reagent may change from a first state (e.g., substantially colorless or nonfluorescent) to a second state (e.g., colored or fluorescent) in and/or surrounding a colony of the target microorganism. In any embodiment, the colonies can be enumerated and, optionally, the number of colonies of target microorganisms can be recorded. In some embodiments, the microorganisms can be counted using an automated system, such as an automated colony counter.

In any embodiment, after sealing the sample port, the method further comprises laying the outer surface of the first wall portion of the device or laying the outer surface of the second wall portion of the device onto a surface that is substantially perpendicular to gravitational force. Advantageously, laying the outer surface of its second wall portion of the device onto a surface that is substantially perpendicular to the force of gravity facilitates flow of the sample liquid through the membrane filter by force of gravity. In addition, laying the outer surface of its second wall portion of the device onto a surface that is substantially perpendicular to the force of gravity facilitates contact between the hydrated cold-water-soluble hydrogel-forming composition adhered to the first wall portion and the membrane filter as the liquid passes through the membrane filter from the first compartment to the second compartment.

In any embodiment, the method further comprises passing at least 90%, at least 92%, at least 95%, at least 97% or at least 98% of the predetermined volume from the first compartment to the second compartment. The portion of the predetermined volume that remains in the first compartment is substantially present as part of the gel formed by hydrating the cold-water-soluble first hydrogel-forming composition.

Various embodiments are described that are devices, kits, methods of making the devices, or methods of detecting and enumerating microorganisms.

Embodiment 1 is a microbial detection device. The device includes a body member including a substrate having a first major surface and a second major surface. The device further includes a substantially dry, first microbial growth nutrient composition disposed on a portion of the first major surface, a first adhesive composition adhered to the first microbial growth nutrient composition, and a cold-water-soluble first hydrogel-forming composition adhered to the first adhesive composition. The device also includes a cover sheet attached to the body member, where the cover sheet includes a first major surface facing the body member.

Embodiment 2 is the device of embodiment 1, further including a substantially dry, second microbial growth nutrient disposed on a portion of the first major surface of the cover sheet.

Embodiment 3 is the device of embodiment 2, wherein the second microbial growth nutrient composition includes a second microbial growth nutrient and at least one cold-water-soluble gelling agent.

Embodiment 4 is the device of embodiment 3, further including a second adhesive composition adhered to the second microbial growth nutrient composition.

Embodiment 5 is the device of embodiment 1, further including a second adhesive composition disposed on a portion of the first major surface of the cover sheet.

Embodiment 6 is the device of embodiment 4 or embodiment 5, further including at least one cold-water-soluble gelling agent adhered to the second adhesive composition.

Embodiment 7 is the device of any of embodiments 4 to 6, wherein the second adhesive composition includes at least one indicator agent.

Embodiment 8 is the device of any of embodiments 4 to 7, wherein the second adhesive composition includes a pressure sensitive adhesive.

Embodiment 9 is the device of any of embodiments 4 to 8, wherein the second adhesive composition includes a solvent based adhesive.

Embodiment 10 is the device of any of embodiments 4 to 9, wherein the second adhesive composition includes an alkyl acrylate copolymer.

Embodiment 11 is the device of any of embodiments 1 to 10, wherein the first adhesive composition includes at least one indicator agent.

Embodiment 12 is the device of any of embodiments 1 to 10, wherein the first adhesive composition includes a pressure sensitive adhesive.

Embodiment 13 is the device of any of embodiments 1 to 12, wherein the first adhesive composition includes a solvent based adhesive.

Embodiment 14 is the device of any of embodiments 1 to 13, wherein the first adhesive composition includes an alkyl acrylate copolymer.

Embodiment 15 is the device of any of embodiments 1 to 14, wherein the first microbial growth nutrient composition includes a first microbial growth nutrient and at least one cold-water-soluble gelling agent.

Embodiment 16 is the device of embodiment 15, wherein the device includes the microbial growth nutrient at a coating weight of 12 mg/in$^2$ or more.

Embodiment 17 is the device of embodiment 15 or embodiment 16, wherein the first microbial growth nutrient includes at least one of a meat peptone, a casein peptone, a gelatin peptone, a soy peptone, a beef extract, a yeast extract, lactose, glucose, dextrose, tryptose, galactose, tryptone, a fat, a mineral, or a vitamin.

Embodiment 18 is the device of any of embodiments 1 to 17, wherein the cold-water-soluble first hydrogel-forming composition comprises a cold-water-soluble gelling agent selected from the group consisting of alginate, carboxymethyl cellulose, tara gum, hydroxyethyl cellulose, hydroxypropyl methylcellulose, guar gum, locust bean gum, xanthan gum, polyacrylamide, polyurethane, polyethylene oxides, and combinations thereof.

Embodiment 19 is a microbial detection device. The microbial detection device includes a water-proof pouch including a first wall portion having an inner surface and an outer surface, a second wall portion having an inner surface and an outer surface, and a porous membrane filter disposed in the pouch between the inner surface of the first wall portion and the inner surface of the second wall portion. The membrane filter has a first major surface and a second major surface opposite the first major surface. The water-proof pouch further includes a first compartment defined in part by the inner surface of the first wall portion and defined in part by the first major surface of the membrane filter and a sealable sample port that provides access to deposit a liquid into the first compartment. Additionally, the water-proof pouch includes a second compartment defined in part by the inner surface of the second wall portion and defined in part by the second major surface of the membrane filter, and an absorbent pad disposed in the second compartment. The membrane filter permits passage of aqueous liquids from the first compartment to the second compartment and prevents passage of particles of a predetermined size from the first compartment to the second compartment. The water-proof pouch also includes a substantially dry microbial growth nutrient composition disposed on a portion of the pouch in the first compartment, an adhesive composition adhered to the microbial growth nutrient composition, and a cold-water-soluble hydrogel-forming composition adhered to the adhesive composition.

Embodiment 20 is the device of embodiment 19, wherein the pouch includes a deformable first wall portion disposed opposite the membrane filter in the first compartment and the microbial growth nutrient composition is disposed on the first wall portion.

Embodiment 21 is the device of embodiment 19, wherein the membrane filter is coupled to a frame, wherein the frame includes an aperture through which liquid passes from the first compartment into the membrane filter, wherein the aperture defines a first area, and wherein the microbial growth nutrient composition disposed on the pouch defines a second area that is greater than or equal to the first area.

Embodiment 22 is the device of any of embodiments 19 to 21, wherein the device is dimensioned to receive a liquid sample having a volume between 25 mL and 150 mL, inclusive.

Embodiment 23 is the device of any of embodiments 19 to 22, wherein the adhesive composition includes at least one indicator agent.

Embodiment 24 is the device of any of embodiments 19 to 23, wherein the adhesive composition includes a pressure sensitive adhesive.

Embodiment 25 is the device of any of embodiments 19 to 24, wherein the adhesive composition includes a solvent based adhesive.

Embodiment 26 is the device of any of embodiments 19 to 25, wherein the adhesive composition includes an alkyl acrylate copolymer.

Embodiment 27 is the device of any of embodiments 19 to 26, wherein the microbial growth nutrient composition includes a microbial growth nutrient and at least one cold-water-soluble gelling agent.

Embodiment 28 is the device of embodiment 27, wherein the device includes the microbial growth nutrient at a coating weight of 12 mg/in$^2$ or more.

Embodiment 29 is the device of embodiment 27 or embodiment 28, wherein the microbial growth nutrient includes at least one of a meat peptone, a casein peptone, a gelatin peptone, a soy peptone, a beef extract, a yeast extract, lactose, glucose, dextrose, tryptose, galactose, tryptone, a fat, a mineral, or a vitamin.

Embodiment 30 is the device of any of embodiments 19 to 29, wherein the cold-water-soluble hydrogel-forming composition includes a cold-water-soluble gelling agent selected from the group consisting of alginate, carboxymethyl cellulose, tara gum, hydroxyethyl cellulose, hydroxypropyl methylcellulose, guar gum, locust bean gum, xanthan gum, polyacrylamide, polyurethane, polyethylene oxides, and combinations thereof.

Embodiment 31 is a method for detecting and enumerating at least one microorganism in a sample. The method includes providing a device according to any of embodiments 1 to 18, separating the first layer from the second layer, and adding a predetermined volume of a sample containing at least one microorganism onto the first hydrogel-forming composition to form an inoculated device. The method further includes contacting the first layer back to the second layer, incubating the inoculated device, and detecting the presence or an absence of a colony of the target microorganism in the device.

Embodiment 32 is a method for detecting and enumerating at least one microorganism in a sample. The method includes providing a device according to any of embodiments 19 to 30, placing a predetermined volume of aqueous sample into the first compartment of the device, sealing the sample port, incubating the device, and detecting the presence or an absence of a colony of the target microorganism in the device.

Embodiment 33 is a microbial detection device. The device includes a body member including a substrate having a first major surface and a cover sheet attached to the body member, wherein the cover sheet comprises a first major surface facing the body member. The device further includes a substantially dry, first microbial growth nutrient composition disposed on a portion of the first major surface of the cover sheet, a first adhesive composition adhered to the first microbial growth nutrient composition, and a cold-water-soluble first hydrogel-forming composition adhered to the first adhesive composition.

Embodiment 34 is the device of embodiment 33, further including a spacer disposed on the first major surface of the substrate.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals are available from chemical suppliers such as Sigma-Aldrich Chemical Company, St. Louis, Mo.

TABLE 1

| Materials | |
| --- | --- |
| Material Name/Description | Source |
| BACTO Tryptic Soy Broth (TSB) | Becton, Dickinson and Company, Franklin Lakes, NJ |
| Guar Gum (Meyprogat 150) | Danisco, Copenhagen, Denmark |

TABLE 1-continued

| Materials | |
| --- | --- |
| Material Name/Description | Source |
| 2,3,5-Triphenyl Tetrazolium Chloride (TTC) | Sigma-Aldrich Corporation, St. Louis, MO |

Incubation and Inoculation

The bacterial strains listed in Table 2 were obtained from MICROBIOLOGICS, Incorporated (St. Cloud, Minn.) and individually incubated overnight in tryptic soy broth (TSB) at 30° C. Inoculums were prepared by serially diluting each culture sample in TSB. For the devices of Examples 1-2, the culture samples were diluted so as to yield a final concentration of about 10-300 colony forming unit (cfu) counts per 1 mL of inoculum. For the device of Example 3, the culture samples were diluted so as to yield a final concentration of about 10-300 colony forming unit (cfu) counts per 100 mL of inoculum.

TABLE 2

| Bacterial Strains |
| --- |
| *Escherichia coli* (ATCC 25922) |
| *Staphylococcus aureus* (ATCC 25923) |
| *Pseudomonas* sp. (ATCC 51821) |
| *Salmonella enterica* (ATCC 51812) |
| *Streptococcus agalactiae* (ATCC 27956) |

Example 1

Preparation of a Microbial Detection Device

Microbial detection devices according to the device of FIG. 1 were constructed (except without a nutrient coating 24 on the cover sheet 22). For each device, the substrate of the body member was a clear, biaxially-oriented polypropylene (BOPP) film (1.6 mil (0.04 mm) thick and corona treated on both sides). One side of the substrate film was sequentially coated with a microbial growth nutrient composition, an adhesive composition, and a guar gum (e.g., cold-water-soluble first hydrogel-forming) composition according to the following procedure.

The microbial growth nutrient coating composition was prepared by vigorously mixing (using an air-driven overhead mixer with a JIFFY-type mixing impeller) 30 g of tryptic soy broth (TSB) and 500 mL of purified water [obtained from a MILLI-Q Gradient Water Purification System (model #ZMQS6V00Y, Merck Millipore Corporation, Billerica, Mass.)] until the TSB was completely dissolved. The resulting solution had a pH of 7.3 (Mettler-Toledo FE20 FiveEasy™ pH Meter, Mettler-Toledo LLC, Columbus, Ohio). Guar gum (10 g) was added to the nutrient solution and vigorous stirring was continued for about 10 minutes. The resulting solution was knife-coated onto one side of the BOPP film substrate with a 14 mil (0.35 mm) gap setting. The nutrient coated substrate was dried in an oven at 85° C. for 12 minutes to provide a dry coat weight of about 360 mg/24 in$^2$ (2.3 mg/cm$^2$).

An isooctyl acrylate/acrylic acid (98/2 weight ratio) pressure-sensitive adhesive (PSA) coating formulation containing TTC (2,3,5-triphenyl tetrazolium chloride) indicator as described in Example 4 of U.S. Pat. No. 5,409,838 (which is incorporated herein by reference) was knife-coated onto the exposed nutrient coating with a 2 mil (0.05 mm) gap setting. The resulting coated film was dried in an oven at 65° C. for 6 minutes to provide a PSA coating having a dry coat weight of about 179 mg/24 in² (1.15 mg/cm²). The adhesive coated side of the substrate was then powder coated with guar gum. The powder was evenly applied and excess powder was removed from the adhesive layer by hand shaking of the film followed by lightly brushing the surface with a paper towel. The final coat weight of the guar gum was about 409 mg/24 in² (2.6 mg/cm²). The resulting powder coated substrate film was cut into 76 mm wide by 102 mm long sections to form the finished body member of the device.

The cover sheet of the device was a clear, BOPP film (1.6 mil (0.04 mm) thick and corona treated on both sides) that was coated on one side with an isooctyl acrylate/acrylic acid (98/2 weight ratio) pressure-sensitive adhesive coating formulation containing TTC as described in Example 4 of U.S. Pat. No. 5,409,838. The adhesive layer was subsequently powder coated with guar gum. The powder was evenly applied and excess powder was removed from the adhesive layer. The coated cover sheet film was cut to match the dimensions of the body member and then attached (in a hinge-like fashion) along one edge (the 76 mm edge) of the body member using double sided adhesive tape. For each device, the cover sheet and the body member were oriented so that the coated surface of the cover sheet faced the coated surface of the body member.

The detection devices were inoculated with a single microbial sample selected from Table 2. The cover sheet of the device was lifted and 1 mL of the inoculum (i.e., final dilution as described above) was added by pipet to the exposed coated surface of the body member. The cover sheet was replaced and the sample was uniformly spread by applying downward pressure with a 3M PETRIFILM Flat Spreader (3M Corporation). The inoculated devices were incubated at 30° C. for 48 hours. The red-colored colonies were counted by visual examination at the end of the incubation period. As comparative examples, commercially available PETRIFILM Aerobic Count (AC) Plates (3M Corporation) were individually inoculated, incubated, and counted in the same manner as with the detection devices. The results are presented in Table 3.

Example 2

Preparation of a Microbial Detection Device

Microbial detection devices according to the device of FIG. 15 were constructed. For each device, the substrate of the body member was a clear, biaxially-oriented polypropylene (BOPP) film (1.6 mil (0.04 mm) thick and corona treated on both sides) that was cut into 76 mm wide by 102 mm long sections. The body member was completed by adhesively laminating a 76 mm wide by 102 mm long polyethylene film spacer (Optimum Plastics, Bloomer, Wis.) to one side of the substrate. The spacer was approximately 20 mil (0.51 mm) thick and contained a 6.0 cm diameter circular opening that was positioned near the center of the spacer. The circular opening defined the perimeter of the sample-receiving zone of the device.

The cover sheet of the device was a clear, biaxially-oriented polypropylene (BOPP) film (1.6 mil (0.04 mm) thick and corona treated on both sides) that was sequentially coated on one side with a microbial growth nutrient composition, an adhesive composition, and a guar gum (e.g. cold-water-soluble first hydrogel-forming) composition according to the following procedure.

The microbial growth nutrient coating composition was prepared by vigorously mixing (using an air-driven overhead mixer with a JIFFY-type mixing impeller) 30 g of tryptic soy broth (TSB) and 500 mL of purified water [obtained from a MILLI-Q Gradient Water Purification System (model #ZMQS6V00Y, Merck Millipore Corporation, Billerica, Mass.)] until the TSB was completely dissolved. The resulting solution had a pH of 7.3 (Mettler-Toledo FE20 FiveEasy™ pH Meter, Mettler-Toledo LLC, Columbus, Ohio). Guar gum (10 g) was added to the nutrient solution and vigorous stirring was continued for about 10 minutes. The resulting solution was knife-coated onto one side of the BOPP cover sheet film with a 14 mil (0.35 mm) gap setting. The nutrient coated film was dried in an oven at 85° C. for 12 minutes to provide a dry coat weight of about 360 mg/24 in² (2.3 mg/cm²).

An isooctyl acrylate/acrylic acid (98/2 weight ratio) pressure-sensitive adhesive (PSA) coating formulation containing TTC (2,3,5-triphenyl tetrazolium chloride) indicator as described in Example 4 of U.S. Pat. No. 5,409,838 (which is incorporated herein by reference) was knife-coated onto the exposed nutrient coating with a 2 mil (0.05 mm) gap setting. The resulting coated film was dried in an oven at 65° C. for 6 minutes to provide a PSA coating having a dry coat weight of about 179 mg/24 in² (1.15 mg/cm²). The adhesive coated side of the cover sheet film was then powder coated with guar gum. The powder was evenly applied and excess powder was removed from the adhesive layer by hand shaking of the film followed by lightly brushing the surface with a paper towel. The final coat weight of the guar gum was about 409 mg/24 in² (2.6 mg/cm²).

The coated cover sheet film was then cut to match the dimensions of the body member. The finished devices were assembled by attaching a cover sheet to a body member (in a hinge-like fashion) along one edge (the 76 mm edge) of the spacer using double sided adhesive tape. For each device, the cover sheet and the body member were oriented so that the coated surface of the cover sheet faced the spacer side of the body member.

The detection devices were inoculated with a single microbial sample selected from Table 2. The cover sheet of the device was lifted and 1 mL of the inoculum (i.e., final dilution as described above) was added by pipet to the exposed coated surface of the body member. The cover sheet was replaced and the sample was uniformly spread by applying downward pressure with a 3M PETRIFILM Flat Spreader (3M Corporation, St. Paul, Minn.). The inoculated devices were incubated at 30° C. for 48 hours. The red-colored colonies were counted by visual examination at the end of the incubation period. The results are presented in Table 3.

Example 3

Preparation of a Microbial Detection Device

A microbial detection device pouch according to FIG. 11 was constructed. The second wall portion consisted of a 127 mm by 152.4 mm piece of clear BOPP film (1.6 mil (0.04 mm) thick and corona treated on both sides). The absorbent pad was a 101.6 mm by 127 mm piece of Gelok 30040-0305 superabsorbent polymer (SAP) laminate (300 g/m² of sodium polyacrylate granules laminated between tissue layers, Gelok Industries, Dunbridge, Ohio). The membrane filter was a 101.6 mm by 127 mm piece of DuraPES® 450 Membrane (5.5 mil (0.14 mm) thick, hydrophilic polyethersulfone membrane for microfiltration obtained from the 3M Corporation). A 101.6 mm by 127 mm piece of Fitesa-ADL2 non-woven material was adhesively laminated between the SAP laminate and membrane using hot melt adhesive (#H4073A, Bostik Company, Milwaukee, Wis.). The resulting laminate was placed and centered on the inner surface of the second wall portion oriented such that the absorbent pad faced the inner surface of the second wall. In the orientation of this construction, a 12.7 mm strip along the perimeter of the inner surface of the second wall portion was not covered.

A frame layer was prepared by first coating one side of a clear BOPP film (1.6 mil (0.04 mm) thick and corona treated on both sides) with an isooctyl acrylate/acrylamide (98/2 weight ratio) pressure sensitive adhesive according to the method described in Example 4 of U.S. Pat. No. 5,409,838. The coated film was subsequently cut to form a frame having external dimensions of 127 mm by 152.4 mm and a centered 76.2 mm by 101.6 mm internal opening. The resulting frame had a 25.4 mm wide adhesively coated border. The frame then was adhesively attached to the membrane filter and the inner surface of the second wall creating a partially constructed device that had a 76.2 mm by 101.6 mm section of the membrane uncovered on one side.

A separate sheet of clear BOPP film (1.6 mil (0.04 mm) thick and corona treated on both sides) was knife-coated with the TSB microbial growth nutrient coating composition described in Example 1 (14 mil (0.35 mm) gap setting). The microbial growth nutrient coated substrate was dried in an oven at 85° C. for 12 minutes to provide a dry coat weight of about 360 mg/24 in$^2$ (2.3 mg/cm$^2$). An isooctyl acrylate/acrylic acid (98/2 weight ratio) pressure-sensitive adhesive coating formulation containing TTC as described in Example 4 of U.S. Pat. No. 5,409,838 was knife-coated onto the exposed nutrient coating with a 2 mil (0.05 mm) gap setting. The resulting coated film was dried in an oven at 65° C. for 6 minutes to provide a PSA coating having a dry coat weight of about 179 mg/24 in$^2$ (1.15 mg/cm$^2$). The adhesive coated side of the film was then powder coated with guar gum (e.g., cold-water-soluble hydrogel-forming composition). The powder was evenly applied and excess powder was removed from the adhesive layer by hand shaking of the film followed by lightly brushing the surface with a paper towel. The final coat weight of the guar gum was about 409 mg/24 in$^2$ (2.6 mg/cm$^2$). This was the same coated substrate section used to prepare the coated substrate for the device described in Example 1. The film sheet was cut into a 76.2 mm wide by 101.6 mm long section and then placed to cover the previously uncovered membrane of the partially constructed device. The film was oriented such that the coated side of the film faced the membrane.

The first wall portion consisted of a 127 mm by 152.4 mm piece clear BOPP film (1.6 mil (0.04 mm) thick and corona treated on both sides) that had been coated on one side with an isooctyl acrylate/acrylamide (98/2 weight ratio) pressure sensitive adhesive according to the method described in Example 4 of U.S. Pat. No. 5,409,838. A 25.4 mm wide piece of silicone coated paper release liner was attached along one of the 127 mm edges on the coated surface of the first wall portion. The first wall portion was then edge aligned with and adhesively laminated to both the uncoated surface of the nutrient coated BOPP film and the surface of the frame layer that faced away from the second wall portion. This construction resulted in a pouch with an opening to a first compartment defined in part by the first wall portion and the membrane filter.

The detection devices were inoculated with a single microbial sample selected from Table 2. The final dilution of the inoculum sample (100 mL, procedure described above) was then poured into the first compartment of a pouch device. The release liner on the pouch was removed and the first compartment was sealed. The device was then placed on a flat, horizontal surface (outer surface of the second wall portion facing the horizontal surface) in an incubator and maintained at 30° C. for 48 hours. The red-colored colonies (cfu) in each device were counted by visual examination at the end of the incubation period. The results are presented in Table 3.

TABLE 3

| | Colony (cfu) Count | | | |
|---|---|---|---|---|
| Organism | Device of Example 1 | Device of Example 2 | Device of Example 3 (Pouch) | PETRIFILM AC Plate (Comparative Example) |
| Escherichia coli (ATCC 25922) | 96 | 85 | 97 | 89 |
| Staphylococcus aureus (ATCC 25923) | 48 | 40 | 59 | 28 |
| Pseudomonas sp. (ATCC 51821) | 58 | 36 | 50 | 37 |
| Salmonella enterica (ATCC 51812) | 110 | 121 | 116 | 102 |
| Streptococcus agalactiae (ATCC 27956) | 18 | 17 | 26 | 21 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A microbial detection device, the device comprising:
a body member comprising a substrate having a first major surface and a second major surface;
a substantially dry, first microbial growth nutrient composition disposed on a portion of the first major surface;
a first adhesive composition adhered to the first microbial growth nutrient composition;
a cold-water-soluble first hydrogel-forming composition adhered to the first adhesive composition; and
a cover sheet attached to the body member, wherein the cover sheet comprises a first major surface facing the body member,
wherein each of the first adhesive composition, the first microbial growth nutrient composition, and the cold-water-soluble first hydrogel-forming composition is in the form of a layer, and wherein the first adhesive composition layer is located between the first microbial growth nutrient composition layer and the cold-water-soluble first hydrogel-forming composition layer.

2. The device of claim 1, further comprising a substantially dry, second microbial growth nutrient disposed on a portion of the first major surface of the cover sheet.

3. The device of claim 2, wherein the second microbial growth nutrient composition comprises a second microbial growth nutrient and at least one cold-water-soluble gelling agent.

4. The device of claim 3, further comprising a second adhesive composition adhered to the second microbial growth nutrient composition.

5. The device of claim 1, further comprising a second adhesive composition disposed on a portion of the first major surface of the cover sheet.

6. The device of claim 4, further comprising at least one cold-water-soluble gelling agent adhered to the second adhesive composition.

7. The device of claim 1, wherein the first adhesive composition comprises a solvent based adhesive.

8. The device of claim 1, wherein the first adhesive composition comprises an alkyl acrylate copolymer.

9. The device of claim 1, wherein the first microbial growth nutrient composition comprises a first microbial growth nutrient and at least one cold-water-soluble gelling agent.

10. A microbial detection device, comprising:
a water-proof pouch comprising:
a first wall portion having an inner surface and an outer surface;
a second wall portion having an inner surface and an outer surface;
a porous membrane filter disposed in the pouch between the inner surface of the first wall portion and the inner surface of the second wall portion, the membrane filter having a first major surface and a second major surface opposite the first major surface;
a first compartment defined in part by the inner surface of the first wall portion and defined in part by the first major surface of the membrane filter;
a sealable sample port that provides access to deposit a liquid into the first compartment;
a second compartment defined in part by the inner surface of the second wall portion and defined in part by the second major surface of the membrane filter;
wherein the membrane filter permits passage of aqueous liquids from the first compartment to the second compartment and prevents passage of particles of a predetermined size from the first compartment to the second compartment;
a substantially dry microbial growth nutrient composition disposed on a portion of the pouch in the first compartment;
an adhesive composition adhered to the microbial growth nutrient composition;
a cold-water-soluble hydrogel-forming composition adhered to the adhesive composition; and
an absorbent pad disposed in the second compartment,
wherein each of the adhesive composition, the substantially dry microbial growth nutrient composition, and the cold-water-soluble hydrogel-forming composition is in the form of a layer, and wherein the adhesive composition layer is located between the substantially dry microbial growth nutrient composition layer and the cold-water-soluble hydrogel-forming composition layer.

11. The device of claim 10, wherein the device is dimensioned to receive a liquid sample having a volume between 25 mL and 150 mL, inclusive.

12. The device of claim 10, wherein the microbial growth nutrient composition comprises a microbial growth nutrient and at least one cold-water-soluble gelling agent.

13. The device of claim 12, wherein the microbial growth nutrient comprises at least one of a meat peptone, a casein peptone, a gelatin peptone, a soy peptone, a beef extract, a yeast extract, lactose, glucose, dextrose, tryptose, galactose, tryptone, a fat, a mineral, or a vitamin.

14. A method for detecting and enumerating at least one microorganism in a sample comprising:
providing a device according to claim 1;
separating the first layer from the second layer;
adding a predetermined volume of a sample containing at least one microorganism onto the first hydrogel-forming composition to form an inoculated device;
contacting the first layer back to the second layer;
incubating the inoculated device; and
detecting the presence or an absence of a colony of the target microorganism in the device.

15. A method for detecting and enumerating at least one microorganism in a sample comprising:
providing a device according to claim 10;
placing a predetermined volume of aqueous sample into the first compartment of the device;
sealing the sample port;
incubating the device; and
detecting the presence or an absence of a colony of the target microorganism in the device.

16. The device of claim 1, wherein the first adhesive composition protects the first microbial growth nutrient composition from washing off when a fluid sample is introduced into the device due to covering the first microbial growth nutrient composition.

* * * * *